US009651471B2

(12) United States Patent
Davis et al.

(10) Patent No.: US 9,651,471 B2
(45) Date of Patent: *May 16, 2017

(54) SYSTEM AND METHOD OF MEASURING DEFECTS IN FERROMAGNETIC MATERIALS

(71) Applicant: The Charles Stark Draper Laboratory, Inc., Cambridge, MA (US)

(72) Inventors: Almir D. Davis, Quincy, MA (US); William J. Trinkle, Arlington, MA (US); Donald Gustafson, Lexington, MA (US); Philip S. Babcock, IV, Westford, MA (US); Richard T. Berthold, Ashland, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 47 days.

This patent is subject to a terminal disclaimer.

(21) Appl. No.: 14/713,503

(22) Filed: May 15, 2015

(65) Prior Publication Data

US 2015/0330946 A1     Nov. 19, 2015

Related U.S. Application Data

(60) Provisional application No. 61/994,961, filed on May 18, 2014.

(51) Int. Cl.
*G01N 17/00* (2006.01)
*G01N 27/82* (2006.01)
*G01N 21/88* (2006.01)

(52) U.S. Cl.
CPC ............. *G01N 17/00* (2013.01); *G01N 27/82* (2013.01); *G01N 2021/8861* (2013.01); *G01N 2021/8864* (2013.01)

(58) Field of Classification Search
CPC ................ G01N 17/00; G01N 27/82; G01N 2021/8864; G01N 2021/8861
See application file for complete search history.

(56) References Cited

U.S. PATENT DOCUMENTS

| 8,447,532 B1 | 5/2013 | Goroshevskiy et al. | ........ 702/42 |
| 8,542,127 B1 | 9/2013 | Goroshevskiy et al. | ..... 340/657 |

(Continued)

FOREIGN PATENT DOCUMENTS

| EP | 2808677 A1 | 12/2014 | ............. G01N 27/85 |
| RU | 2 264 617 C2 | 11/2005 | ............. G01N 27/82 |

(Continued)

OTHER PUBLICATIONS

Ahmad, et al., "A Survey of Low Duty Cycle MAC Protocols in Wireless Sensor Networks," Emerging Communications for Wireless Sensor Networks, InTech Open, 23 pages, Feb. 2011.

(Continued)

*Primary Examiner* — David M Gray
*Assistant Examiner* — Michael Harrison
(74) *Attorney, Agent, or Firm* — Sunstein Kann Murphy & Timbers LLP

(57) ABSTRACT

Defects in ferromagnetic materials are detected and characterized by analyzing the items' magnetic fields to find portions of the magnetic fields that differ in characteristic ways from residual magnetic fields generated by non-defective portions of the items. The portions of the magnetic fields that differ in the characteristic ways correspond to locations of the defects. The residual magnetic fields correspond to portions of the items distant from the defects. The defect characterization may include volume of material lost due to each defect and/or width and/or depth of each defect.

19 Claims, 21 Drawing Sheets

(56) References Cited

U.S. PATENT DOCUMENTS

| | | | |
|---|---|---|---|
| 8,949,042 B1 | 2/2015 | Goroshevskiy et al. | 702/38 |
| 2002/0116980 A1 | 8/2002 | Kerr et al. | 73/1.14 |
| 2007/0115821 A1 | 5/2007 | Sim et al. | 370/231 |
| 2013/0027029 A1 | 1/2013 | Goroshevskiy et al. | 324/228 |
| 2014/0293850 A1 | 10/2014 | Huang et al. | 370/311 |
| 2014/0336937 A1* | 11/2014 | Hallundbæk | E21B 47/0002 702/8 |
| 2015/0042323 A1* | 2/2015 | Freear | G01N 27/82 324/240 |

FOREIGN PATENT DOCUMENTS

| | | | |
|---|---|---|---|
| RU | 2264617 C2 | 11/2005 | G01N 27/82 |
| WO | WO 2013/019136 A1 | 2/2013 | F17D 5/06 |
| WO | WO 2013/128210 A1 | 9/2013 | G01N 27/82 |

OTHER PUBLICATIONS

Basu, et al., "Effect of Overhearing Transmissions on Energy Efficiency in Dense Sensor Networks," IPSN'04, 9 pages, Apr. 26-27, 2004.

De, et al., "ActSee: Activity-Aware Radio Duty-Cycling for Sensor Networks in Smart Environments," Department of Computer Science, Georgia State University, 8 pages, 2011.

Du, et al., "RMAC: A Routing-Enhanced Duty-Cycle MAC Protocol for Wireless Sensor Networks," Department of Computer Science, Rice University, pp. 1478-1486, 2007.

Dunkels, "The ContikiMAC Radio Duty Cycling Protocol," SICS Technical Report, T2011:13, ISSN 1100-3154, pp. 1-11, Dec. 2011.

Hashemi, et al., "Intra-Car Multihop Wireless Sensor Networking: A Case Study," Automotive Networking and Applications, IEEE Communications Magazine, vol. 52, No. 12, pp. 183-191, Dec. 2014.

Ilyas, et al., "Handbook of Sensor Networks: Compact Wireless and Wired Sensing Systems," CRC Press, 3 pages, 2005.

Jawhar, et al., "Ferry-Based Linear Wireless Sensor Networks," College of Information Technology, UAE University, pp. 1-6, 2013.

Jawhar, et al., "Linear wireless sensor networks: Classification and applications," Journal of Network and Computer Applications, vol. 34, pp. 1671-1682, 2011.

Jin, et al., "Monitoring of Distributed Pipeline Systems by Wireless Sensor Networks," Proceedings of the 2008 IAJC-IJME International Conference, 10 pages, 2008.

Karl, et al., "Protocols and Architectures for Wireless Sensor Networks," John Wiley & Sons, 5 pages, Oct. 8, 2007.

Léone, "Radio duty cycling," https://github.com/contiki-os/contiki/wiki/Radio-duty-cycling, 7 pages, Jul. 29, 2014.

Ludovici, et al., "Forwarding Techniques for IP Fragmented Packets in a Real 6LoWPAN Network," Sensors 2011, vol. 11, pp. 992-1008, Jan. 18, 2011.

Mohamed, et al., "Sensor Network Architectures for Monitoring Underwater Pipelines," Sensors 2011, vol. 11, pp. 10738-10764, Nov. 15, 2011.

Pasadas, et al., "Handheld Instrument to Detect Defects in Conductive Plates with a Planar Probe," 2011 IEEE International Instrumentation and Measurement Technology Conference, pp. 1-6, May 2011.

Sadeghioon, et al., "SmartPipes: Smart Wireless Sensor Networks for Leak Detection in Water Pipelines," Journal of Sensor and Actuator Networks, ISSN 2224-2708, vol. 3, pp. 64-78, Feb. 20, 2014.

Tiporlini, et al., "High Sensitivity Optically Pumped Quantum Magnetometer," The Scientific World Journal, vol. 2013, Article ID 858379, pp. 1-8, May 2, 2013.

Valliappan, "Wireless: What is clear channel assessment (CCA)?," Quora, http://www.quora.com/Wireless/What-is-clear-channel-assessment-CCA, 2 pages, Mar. 7, 2013.

Weiss, et al., "The importance of low power sensing for the Internet of Things," Dust Networks Product Group, Linear Technology Corp., 4 pages, Oct. 5, 2013.

Xu, et al., "On Localized Prediction for Power Efficient Object Tracking in Sensor Networks," Distributed Computing Systems Workshops, Proceedings, $23^{rd}$ International Conference, pp. 434-439, May 19, 2003.

Zimmerling, et al., "Energy-Efficient Routing in Linear Wireless Sensor Networks," IEEE Xplore, 3 pages, Nov. 19, 2008.

Rohrback Cosasco Systems, Inc., "Quicksand™ Erosion Detection System," Rohrback Cosasco Systems, Inc., Bulletin No. 700-J, 3 pages, Mar. 15, 2012.

Rohrback Cosasco System, Inc., "Cosasco® Wireless Best Practices: A Guide for Planning, Installation, and Commissioning," Rohrback Cosasco Systems, Inc., Bulletin No. AN-119, 8 pages, May 11, 2011.

Rohrback Cosasco Systems, Inc., "Quicksand™ Wireless Transmitter MWT-3905-QS," Rohrback Cosasco Systems, Inc., Bulletin No. 160-G, 6 pages, Jun. 27, 2012.

Wikipedia, Wireless sensor network, Wikipedia, https://en.wikipedia.org/w/index.php?title=Wireless_sensor_network&oldid=606602738 , 9 pages, May 1, 2014.

Wikipedia, Energy harvesting, Wikipedia, https://en.wikipedia.org/w/index.php?title=Energy_harvesting&oldid=607544418, 10 pages, May 7, 2014.

Wikipedia, Ad hoc On-Demand Distance Vector Routing, Wikipedia, http://en.wikipedia.org/wiki/Ad_hoc_On-Demand_Distance_Vector_Routing, 3 pages, Aug. 7, 2014.

Wikipedia, Mesh networking, Wikipedia, http://en.wikipedia.org/wiki/Mesh_networking, 6 pages, Sep. 19, 2014.

Wikipedia, 6LoWPAN, Wikipedia, https://en.wikipedia.org/wiki/6LoWPAN, 4 pages, Aug. 20, 2014.

Wikipedia, Magnetostriction, Wikipedia, http://en.wikipedia.org/wiki/Magnetostriction, 2 pages, May 8, 2014.

International Searching Authority, International Search Report—International Application No. PCT/US2015/031092, dated Aug. 27, 2015, together with the Written Opinion of the International Searching Authority, 11 pages.

* cited by examiner

SYSTEM AND METHOD OF MEASURING DEFECTS IN FERROMAGNETIC MATERIALS

CROSS-REFERENCE TO RELATED APPLICATIONS

This application claims the benefit of U.S. Provisional Patent Application No. 61/994,961, filed May 18, 2014, titled "System and Method of Measuring Defects in Ferromagnetic Materials," the entire contents of which are hereby incorporated by reference herein, for all purposes.

TECHNICAL FIELD

The present invention relates to defect detection in ferromagnetic materials and, more particularly, to defect detection in ferromagnetic materials using a magnetometer.

BACKGROUND ART

Ferromagnetic materials, such as iron, nickel, steel and other materials, are used to make many items, such as pipes, beams and ocean vessel hulls. As used herein, "ferromagnetic material" includes both ferromagnetic and ferrimagnetic material. In many cases, these materials are subject to corrosion and/or erosion. As used herein, corrosion means loss of material as a result of chemical reaction, most commonly oxidation. As used herein, erosion means loss of material as a result of a mechanical process, such as abrasion. For example, sand produced in an oil or gas well can abrade the inside of a pipeline carrying oil or gas from the well. Material loss due to corrosion and/or erosion is collectively referred to herein as a "defect." As used herein, the term defect also includes a crack, or a void or inclusion of foreign material, such as might occur during manufacture or later. If allowed to occur beyond a critical point, corrosion or erosion may compromise structural integrity of an item, possibly resulting in a catastrophic failure, such as an oil spill, building collapse or ship sinking.

Various apparatus and methods have been used in the prior art in attempts to detect defects in ferromagnetic materials and items made of ferromagnetic materials. Some of these apparatus and methods require removing thermal insulation and striping off corrosion inhibiting surface treatments to gain direct access to a surface of the ferromagnetic material. In some cases, the surface must be polished to create a pristine interface to a sensor or wave propagation from the sensor. These steps are costly, time-consuming and often compromise the thermal insulation and/or the surface treatments.

All prior art apparatus and methods for detecting defects in ferromagnetic materials known to the inventors involve introducing energy into the material. For example, acoustic sensors send a sound wave into the material and measure the signal that returns. Guided-wave and topographic sensors similarly send electromagnetic waves into the material and sense reflections or transport times of the wave. In a different view of imparting energy into the item being measured, Rohrback Cosasco Systems, Inc. produces a line of sand erosion detection probes under the tradename "Quicksand." These probes do not directly measure erosion of pipes, etc. Instead, these probes are sacrificial, in that they detect erosion of portions of the probes themselves. Systems based on such probes assume pipes and other items erode at approximately the same rate as the probes' sacrificial portions. Furthermore, the probes rely on flow of fluid through the pipe, therefore requiring energy to be introduced into the pipe in the form of fluid flow. These systems can detect erosion only inside a pipe. These systems cannot detect defects elsewhere, such as inside the pipe wall or on an outside surface of a pipe, nor can they infer the condition of a pipe due to erosion before the sensor was in place.

Some prior art apparatus and methods involve magnetometry in attempts to detect defects in ferromagnetic materials. For example, U.S. Pat. Nos. 8,542,127 and 8,447,532, both by Valerian Goroshevskiy, et al., disclose using the inverse magnetostrictive Villari effect. The inverse magnetostrictive Villari effect involves changes in a material's magnetic susceptibility under applied mechanical stress. If a pipe suffers a defect, the pipe's magnetic susceptibility when the pipe material is mechanically stressed, for example when the pipe is pressurized, is different than when the pipe is not mechanically stressed. The Goroshevskiy patents rely on detecting this change in magnetic susceptibility as pressure within the pipe changes. Thus, energy must be introduced into the pipe in the form of pressurizing the inferior of the pipe. Some items, such as pipes, remain unused, and therefore unpressurized, for periods of time during which defects may develop. Other structures, such as ship hulls or structural elements, do not lend themselves to known pressurization cycling. However, without pressurization, the Goroshevskiy apparatus and methods cannot detect these defects. Furthermore, Goroshevskiy can determine a defect's location only along the length of a pipe; Goroshevskiy cannot determine the defect's location circumferentially around the pipe.

SUMMARY OF EMBODIMENTS

An embodiment of the present invention provides a system for detecting defects in a ferromagnetic material. The system includes a plurality of magnetometers. The plurality of magnetometers is disposed about a surface of the ferromagnetic material. The plurality of magnetometers senses a magnetic field generated by the ferromagnetic material. The plurality of magnetometers generates magnetic field data, based on the sensed magnetic field. Each magnetometer of the plurality of magnetometers is fixed in position, relative to the ferromagnetic material. The system also includes a magnetic field mapper. The magnetic field mapper generates data points of a two-dimensional map from the magnetic field data. Each data point corresponds to a respective location on the surface of the ferromagnetic material. Each data point represents strength of the sensed magnetic field proximate the location. "Proximate" in this context means close enough so the location of a defect can be determined in both x and y directions, i.e., longitudinally along the ferromagnetic material and laterally across the material. In some embodiments, proximate means within about 5-10 inches. The system also includes a pattern matcher. The pattern matcher identifies, in the map, a plurality of data points that conform to a predefined spatial pattern of magnetic field strength. The pattern matcher outputs a location proximate the surface of the ferromagnetic material that corresponds to the plurality of data points. The outputted location is a location of a defect.

The system may also include a defect size estimator. The defect size estimator estimates a volume of material missing from the ferromagnetic material at the location proximate the surface of the ferromagnetic material. The missing volume estimate is based on amplitude of a feature represented by data in the plurality of data points.

The defect size estimator may estimate an area of the missing material, based on length in two spatial directions of a feature represented by data in the plurality of data points.

The defect size estimator may estimate a depth of the missing material, based on the estimated volume of missing material and length in two spatial directions of a feature represented by data in the plurality of data points.

The system may also include a residual magnetic field strength calculator. The residual magnetic field strength calculator determines amplitude of the magnetic field generated by the ferromagnetic material at a location distant from the location proximate the surface of the ferromagnetic material. The amplitude of the magnetic field is based on at least one of the data points of the map. The system may also include a defect size estimator. The defect size estimator estimates a volume of material missing from the ferromagnetic material at the location proximate the surface of the ferromagnetic material. The volume estimate is made according to amplitude of data in the plurality of data points and the amplitude of the magnetic field generated by the ferromagnetic material at the a location distant from the location proximate the surface of the ferromagnetic material.

The defect size estimator may estimate an area of the missing material, based on length in two spatial directions of a feature represented by data in the plurality of data points.

The defect size estimator may estimate a depth of the missing material, based on the estimated volume of missing material and length in two spatial directions of a feature represented by data in the plurality of data points.

Each magnetometer of the plurality of magnetometers may include three orthogonally oriented magnetometers. Each data point of the map may represent strength of the sensed magnetic field in each of three orthogonal directions. The pattern matcher may identify, for each of the three orthogonal directions, a plurality of data points that conform to a predefined spatial pattern of magnetic field strength and a location proximate the surface of the ferromagnetic material that corresponds to the plurality of data points. The pattern matcher may thereby identifying three locations proximate the surface of the ferromagnetic material. The system may also include a combiner. The combiner may calculate a refined location proximate the surface of the ferromagnetic material from the three identified locations and outputs the refined location.

The pattern matcher may calculate a plurality of spatial derivative values from the data points of the map. The pattern matcher may identify the plurality of data points that conform to the predefined spatial pattern of magnetic field strength from the plurality of spatial derivative values.

The plurality of data points that conform to the predefined spatial pattern of magnetic field strength may corresponds to a loss of a portion of the ferromagnetic material due to corrosion or erosion.

The plurality of data points that conform to the predefined spatial pattern of magnetic field strength corresponds to a crack in the ferromagnetic material.

Another embodiment of the present invention provides a method for detecting defects in a ferromagnetic material. The method includes sensing a magnetic field generated by the ferromagnetic material. Data points of a two-dimensional map are generated from the sensed magnetic field. Each data point corresponds to a respective location on the surface of the ferromagnetic material. Each data point represents strength of the sensed magnetic field proximate the location. In the two-dimensional map, a plurality of data points is identified. The plurality of data points conforms to a predefined spatial pattern of magnetic field strength. A location proximate the surface of the ferromagnetic material is output. The location corresponds to the plurality of data points. The location corresponds to a defect.

Sensing the magnetic field may include disposing a plurality of magnetometers about a surface of the ferromagnetic material. Each magnetometer of the plurality of magnetometers is fixed in position, relative to the ferromagnetic material.

Sensing the magnetic field may include physically scanning the ferromagnetic material with at least one magnetometer by moving the at least one magnetometer, relative to the ferromagnetic material.

Moving the at least one magnetometer, relative to the ferromagnetic material, may include disposing a one-dimensional array of at least two magnetometers along a shape oriented substantially perpendicular to an axis of the ferromagnetic material. The one-dimensional array of at least two magnetometers may be moved along the axis of the ferromagnetic material.

Optionally, a volume of material missing from the ferromagnetic material at the location proximate the surface of the ferromagnetic material may be estimated. The estimate may be based on amplitude of a feature represented by data in the plurality of data points.

Optionally, amplitude of the magnetic field generated by the ferromagnetic material at a location distant from the location proximate the surface of the ferromagnetic material may be determined, based on at least one of the data points of the map. A volume of material missing from the ferromagnetic material at the location proximate the surface of the ferromagnetic material may be estimated, according to amplitude of data in the plurality of data points and the amplitude of the magnetic field generated by the ferromagnetic material at a location distant from the location proximate the surface of the ferromagnetic material.

Optionally, an area of the missing material may be estimated. The estimate may be based on length in two spatial directions of a feature represented by data in the plurality of data points.

A circumference depth of the missing material may be estimated. The estimate may be based on the estimated volume of missing material and length in two spatial directions of a feature represented by data in the plurality of data points.

Sensing the magnetic field may include sensing the magnetic field with a plurality of magnetometers. Each magnetometer of the plurality of magnetometers may include three orthogonally oriented magnetometers. Generating the data points may include generating the data points such that each data point of the map represents strength of the sensed magnetic field in each of three orthogonal directions. Identifying the plurality of data points that conform to the predefined spatial pattern may include, for each of the three orthogonal directions, identifying a plurality of data points that conform to a predefined spatial pattern of magnetic field strength and a location proximate the surface of the ferromagnetic material that corresponds to the plurality of data points, thereby identifying three locations proximate the surface of the ferromagnetic material. In addition, a refined location proximate the surface of the ferromagnetic material may be calculated from the three identified locations. Outputting the location may include outputting the refined location.

A plurality of spatial derivative values may be calculated from the data points of the map. Identifying the plurality of data points that conform to a predefined spatial pattern may include identifying a plurality of data points that conform to the predefined spatial pattern of magnetic field strength from the plurality of spatial derivative values.

Identifying the plurality of data points that conform to a predefined spatial pattern may include identifying a plurality of data points that corresponds to a loss of a portion of the ferromagnetic material due to corrosion or erosion.

Identifying the plurality of data points that conform to a predefined spatial pattern may include identifying a plurality of data points that corresponds to a crack in the ferromagnetic material.

Yet another embodiment of the present invention provides a computer program product for detecting defects in a ferromagnetic material. The computer program product includes a non-transitory computer-readable medium. Computer readable program code is stored on the medium. The computer readable program code includes a sense module, a data point generator module, a defect identifier module and a defect location output module.

The sense module receives magnetic field data from a plurality of magnetometers disposed about a surface of the ferromagnetic material. The plurality of magnetometers sense a magnetic field generated by the ferromagnetic material. The plurality of magnetometers also generates the magnetic field data. The magnetic field data is based on the sensed magnetic field. Each magnetometer of the plurality of magnetometers is fixed in position, relative to the ferromagnetic material.

The data point generator module generates data points of a two-dimensional map from the sensed magnetic field. Each data point corresponds to a respective location on the surface of the ferromagnetic material. Each data point represents strength of the sensed magnetic field proximate the location.

The defect identifier module identifies, in the two-dimensional map, a plurality of data points that conform to a predefined spatial pattern of magnetic field strength. The defect location output module outputs a location proximate the surface of the ferromagnetic material that corresponds to the plurality of data points.

BRIEF DESCRIPTION OF THE DRAWINGS

The invention will be more fully understood by referring to the following Detailed Description of Specific Embodiments in conjunction with the Drawings, of which.

DETAILED DESCRIPTION OF SPECIFIC EMBODIMENTS

Figure 1:
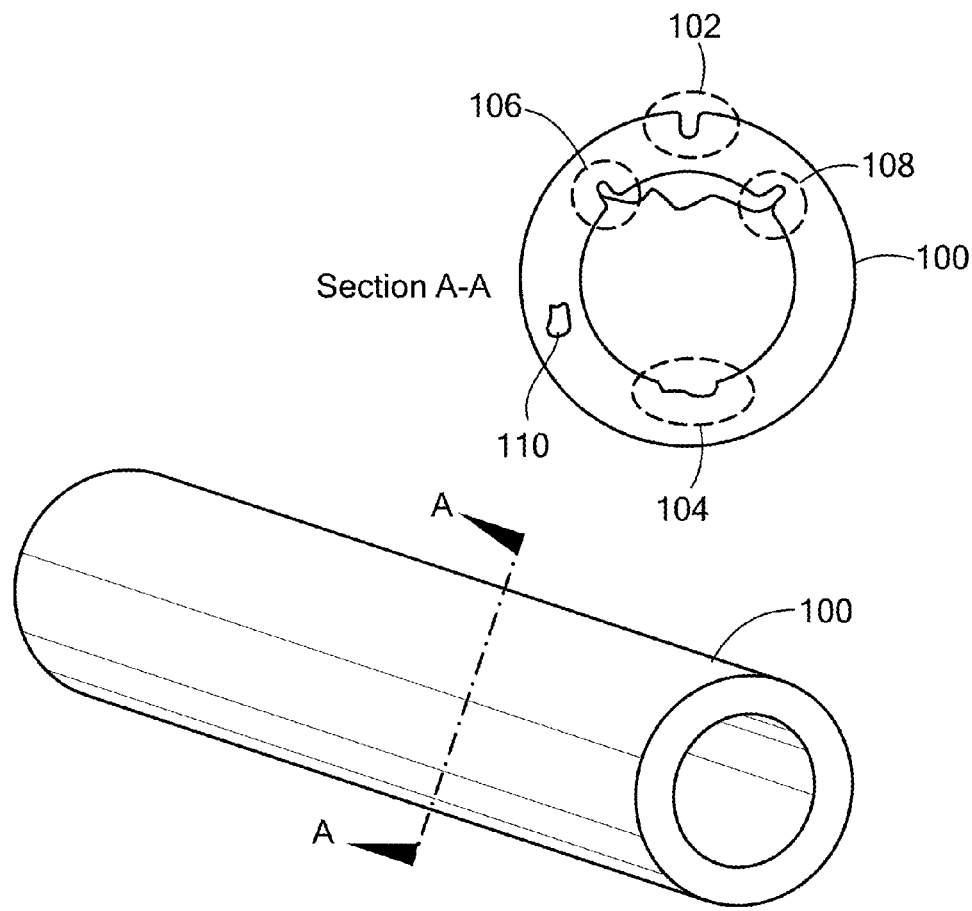
FIG. 1 is a perspective view of a hypothetical pipe and a cross-sectional view of a portion of the pipe, as known in the prior art.

Embodiments of the present invention enable detecting defects in items containing ferromagnetic materials without requiring energy to be introduced into the materials and without necessarily removing thermal insulation, surface treatments and the like from the materials or items. The ferromagnetic materials in the items generate magnetic fields. Embodiments of the present invention detect and characterize defects in the items by analyzing the items' magnetic fields to find portions of the magnetic fields that differ in characteristic ways from residual magnetic fields generated by non-defective portions of the items. The portions of the magnetic fields that differ in the characteristic ways correspond to locations of the defects. The residual magnetic fields correspond to portions of the items distant from the defects. The defect characterization may include volume of material lost due to each defect and/or width and/or depth of each defect. A challenge to any magnetometric approach is that the intrinsic residual magnetic field of the item is typically non-homogeneous, reflective of material and manufacturing variations across the item. A key challenge for these methods is to separate the magnetic "signature" of the defect from the "noise" intrinsic in the item's residual field.

Overview

In some embodiments, a two-dimensional array of magnetometric sensors is disposed parallel to an outside surface of an item to be analyzed. The array of magnetometric sensors collects data enabling the creation of a two-dimensional map of magnetometric data (magnetic field map). In this context, a "mat" of magnetometric sensors wrapped around a circular cross-section pipe or other non-planar item is considered to be two-dimensional.

In some embodiments, an item is physically scanned along one dimension by a one-dimensional array of magnetometric sensors, thereby creating a two-dimensional map of magnetometric data. In some embodiments, an item is raster, spiral or otherwise scanned along more than one dimension by a single magnetometric sensor or a small group of magnetometric sensors to create a two-dimensional map of magnetometric data.

The ferromagnetic material in the item generates a magnetic field. Magnetic fields are vector quantities characterized by both strength and direction. The map of magnetometric data (magnetic field map) represents strength of the magnetic field at each of many points above the surface of the item. A magnetic field map can indicate one, two or three components of the 3-dimensional magnetic field strength vector.

In some embodiments, the magnetometric data is essentially searched for any of several predefined patterns (shapes). A region in which the strength of the magnetic field, or any of the components of the 3-dimensional magnetic field, spatially varies according to one of the predefined patterns corresponds to a location of a defect. According to one of these predefined patterns, along a straight line, the magnetic field begins at the residual level, and then increases in strength to a peak, relative to the residual, then decreases in strength to a valley below the residual, and then returns to the residual level, somewhat similar to the shape of one cycle of a sine curve.

According to another one of these predefined patterns, along the straight line, the magnetic field begins at the residual level, and then increases in strength to a peak, relative to the residual, then decreases in strength to a valley below the residual, and then increases in strength to a second peak, relative to the residual, and then returns to the residual level, somewhat similar to the shape of one and a half cycles of a cosine curve.

As noted, the residual magnetic field corresponds to portions of an item distant from any defect. However, the residual field has many features, due to the item being not perfectly homogeneous, that may mask the presence of a defect signature. By searching the magnetic field measurements for defect signatures, we can identify the location of the defects as compared to the non-defect features in the residual. We refer to this type of analysis, in which magnetic fields of the defect(s) are distinguished from the residual as the means to detect defects, as "spatial analysis."

In some embodiments, the magnetometric data for the item is captured when the item is new or at some other reference point in time. The magnetometric data is stored, and then later, magnetometric data is again captured for the same portion of the item, and the two datasets are compared. Differences between the two datasets represent candidate defects. We refer to this type of analysis, in which data sets captured at different times to determine differences between the datasets, as "temporal analysis." The candidate defects may then be analyzed for defect signatures, as in the spatial analysis.

In some embodiments, multiple arrays of magnetometric sensors are attached to an item to be analyzed and remain attached to the item for essentially the life of the item or for another extended period of time. Each such array is attached at a discrete location on the item. Each array may include an energy harvester to provide electrical power to operate the array. The arrays may be interconnected by a wired or wireless network. The network may employ a messaging protocol, a routing algorithm, clock management and other aspects that enable a linear network that includes hundreds of nodes with greater than ten hops to operate while consuming very little power, i.e., able to be powered by energy harvesters.

The arrays of magnetometric sensors send data, via the network, to a base station, which analyzes the data to detect defects. The base station may be coupled to a distributed control system, plant management system or another external system. The external system may query the base station about defects or command the base station to initiate defect detection. Optionally or alternatively, the base station may notify the external system of defects without a query from the external system. Similarly, the base station may raise an alarm, such as illuminating a light, sounding a horn, sending an e-mail message or initiating a telephone call and playing a pre-recorded or voice synthesized message, if it detects a defect.

As noted, an array of magnetometric sensors may be fixed to an item to collect magnetometric data, or items may be physically scanned by moving magnetometric sensors relative to the items to collect the magnetometric data. In either case, the magnetometric data may be analyzed temporally or spatially to detect defects.

Defects

As noted, defects may be losses of material due to corrosion and/or erosion. Examples and embodiments are described herein in the context of pipes. However, these embodiments and examples apply to other types of items, such as flat sheets, hulls of ships, storage tanks/vessels, beams, columns, etc.

FIG. 1 is a schematic illustration of a hypothetical pipe 100 and a cross section (Section A-A) of the pipe 100. Almost any pipe is subject to developing defects as a result of corrosion or erosion on the outside surface of the pipe, as exemplified at 102, for example as a result of acid rain, chemical spill or accidental or malicious physical damage. Most pipes are also subject to developing defects on inside surfaces of the pipes, as exemplified at 104, 106 and 108. For example, sand produced in an oil or gas well is typically transported along the bottom of a pipe and can, therefore, abrade the bottom of the pipe, as exemplified at 104. Areas of the inside wall of a pipe, where the top surface of liquid within the pipe meets the inside wall of the pipe, exemplified at 106 and 108, are common locations for corrosion. A pipe may also develop defects within the thickness of the pipe's wall, as exemplified at 110.

Figure 2:
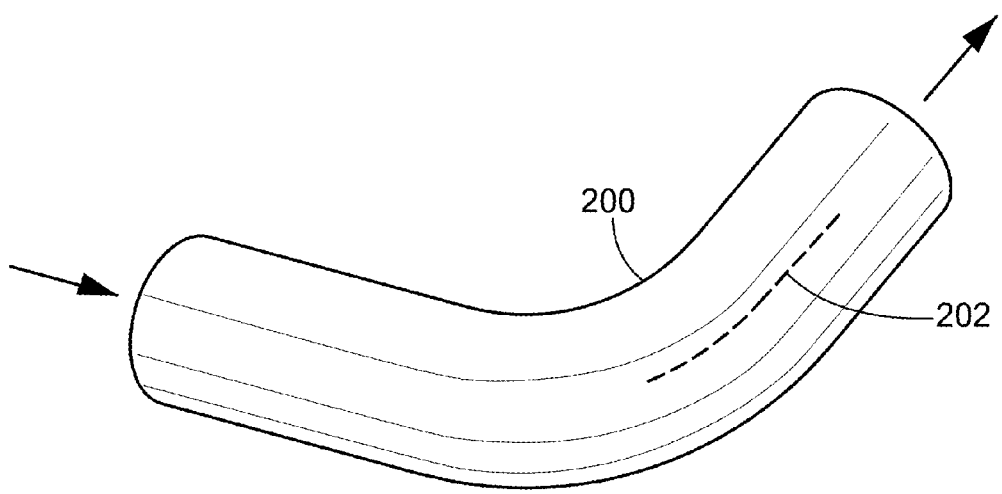
FIG. 2 is a perspective view of a hypothetical curved pipe, as known in the prior art.

Erosion often occurs within and slightly downstream of a bend in a pipe 200, at a location indicated by dashed line 202 in FIG. 2. Turbulence due to the change of flow direction creates candidate sites for corrosion. Arrows indicate a direction of flow within the pipe 200. Enlargements and constrictions in pipelines (not shown) not only create potential sites for erosion, they also tend to create turbulence downstream and, therefore, tend to cause defects adjacent the turbulent regions.

Magnetometers and Defect Detection

Figure 3:
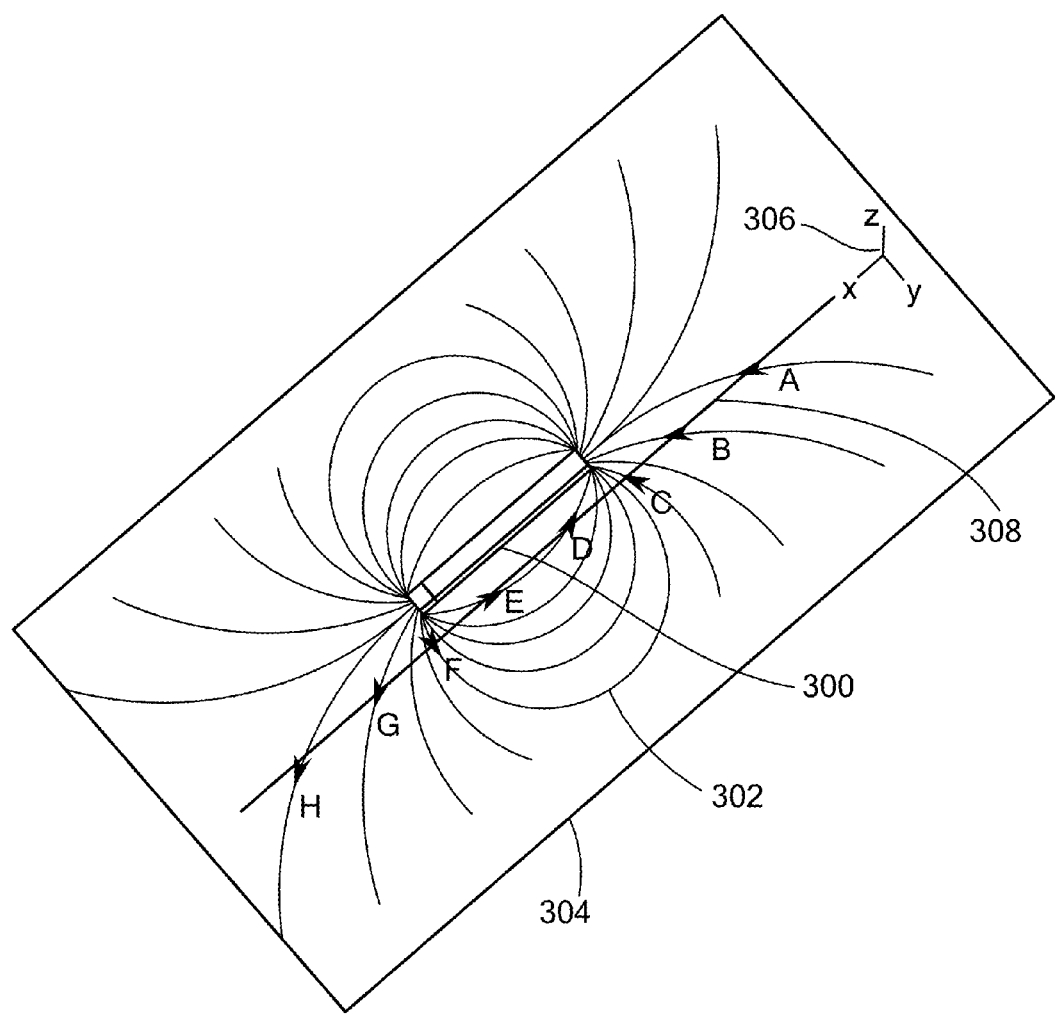
FIG. 3 schematically illustrates a magnetic field produced by a hypothetical magnetic dipole, as known in the prior art.

FIG. 3 schematically illustrates a magnetic field produced by a hypothetical magnetic dipole 300. Magnetic field lines, exemplified by line 302, represent the magnetic field. The magnetic dipole 300 lies in a plane 304 and, for simplicity, only magnetic field lines 300 in the plane 304 are shown.

Figure 4:
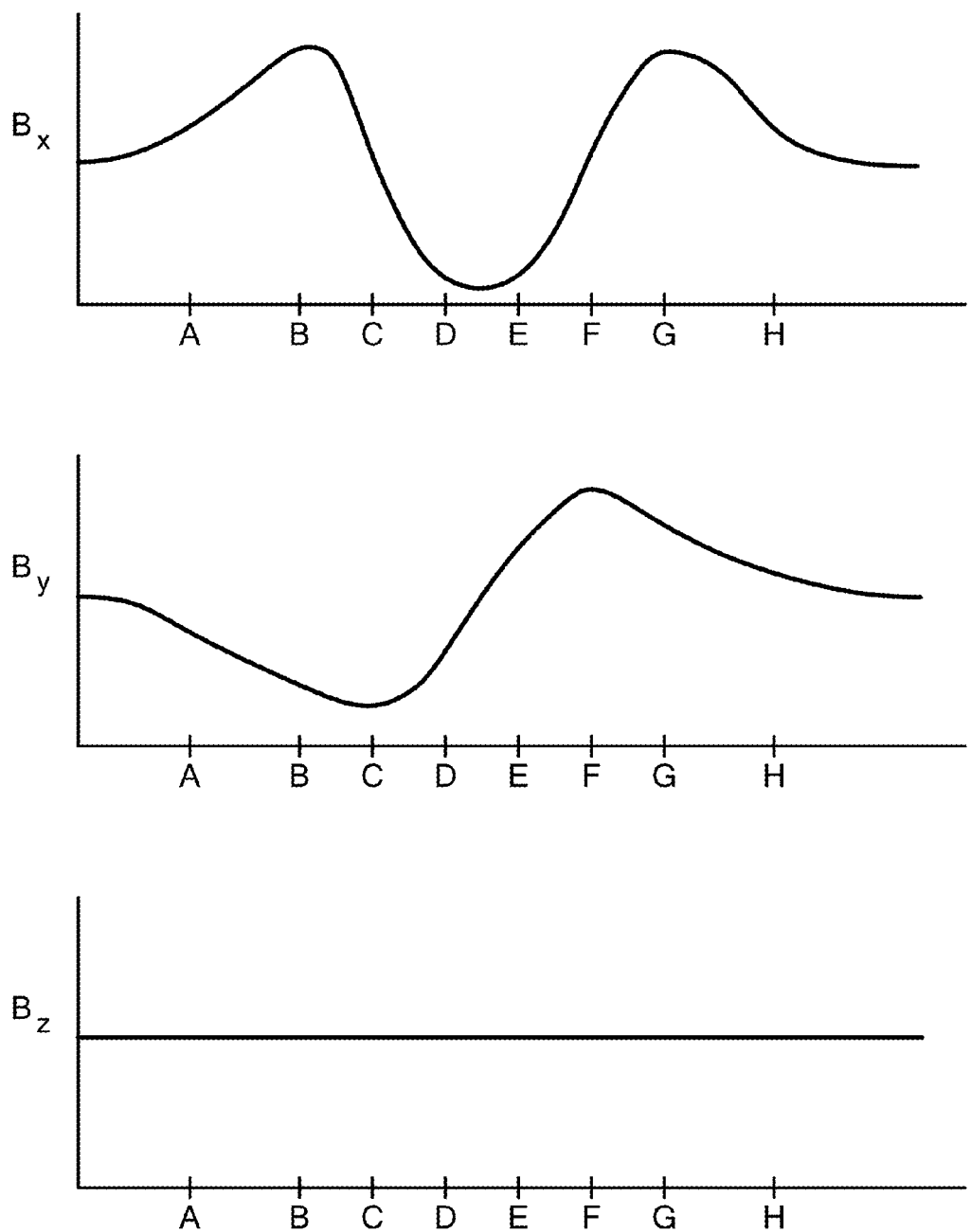
FIG. 4 contains graphs of hypothetical exemplary field strengths Bx, By and Bz sensed by a magnetometer along three axes along a line in FIG. 3.

Vector magnetometers measure vector components of a magnetic field. That is, a vector magnetometer measures strength of a magnetic field that is directed along an axis of the magnetometer. A 3-axis magnetometer 306 measures magnetic field strength along three axes, X, Y and Z. If the magnetometer 306 translates along a line 308 parallel to the magnetic dipole 302, the magnetometer 306 senses a varying magnetic field along the line 308. For example, the X axis sensor senses various field strengths, which represent X components of the magnetic vectors represented by arrows at A, B, C, D, E, F, G and H. FIG. 4 contains graphs of hypothetical exemplary field strengths Bx, By and Bz sensed by the magnetometer 306 along the three axes along the line 308. Note that the Bx graph resembles a cosine curve and the Bz graph resembles a sine curve. These shapes are characteristic of a magnetic field in the vicinity of a discrete magnetic dipole.

Figure 5:
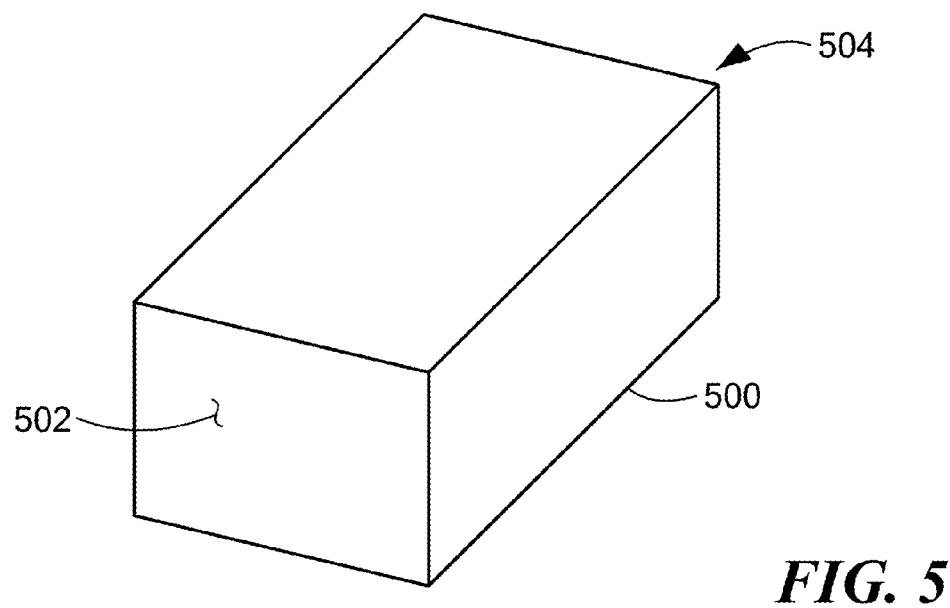
FIG. 5 schematically illustrates a hypothetical plate of ferromagnetic material, as known in the prior art.
Figure 6:
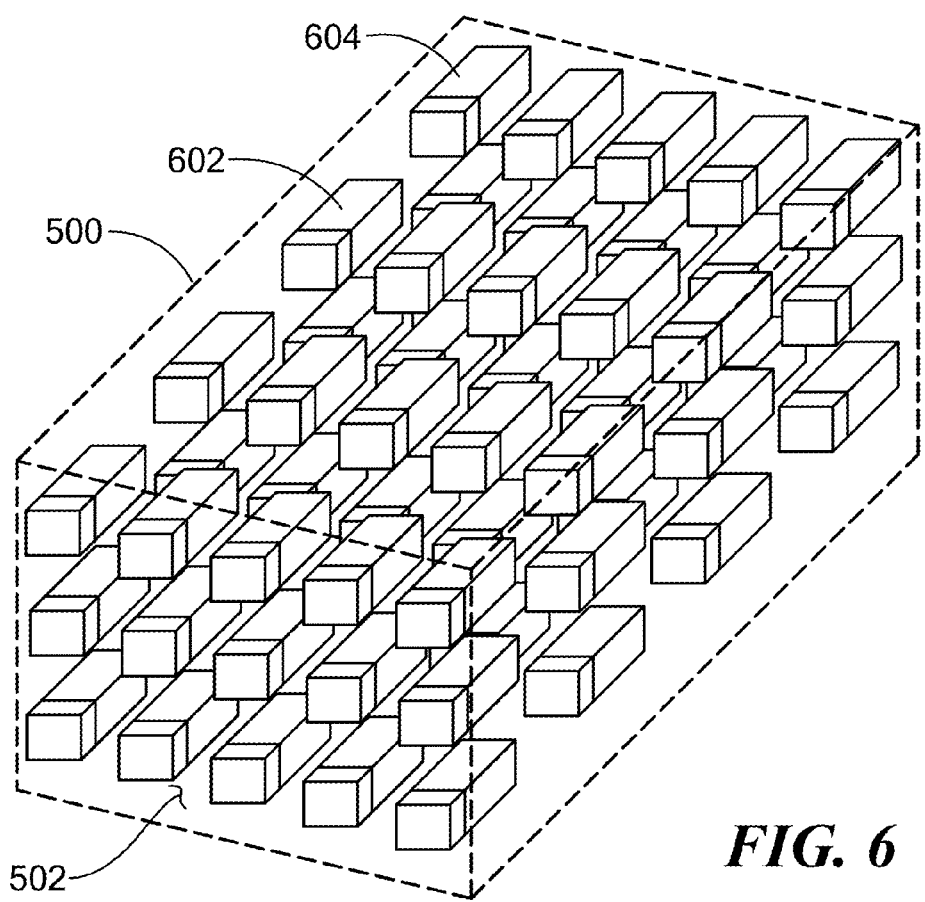
FIG. 6 schematically illustrates the plate of FIG. 5 as many small aligned magnetic dipoles, as interpreted according to embodiments of the present invention.

FIG. 5 schematically illustrates a hypothetical plate of ferromagnetic material 500. The plate 500 may be considered to be composed of many small aligned magnetic dipoles, exemplified by magnetic dipoles 602 and 604, as schematically illustrated in FIG. 6. The magnetic field lines extend from each small magnetic dipole to its front and back neighbors, largely in straight lines, and the magnetic field lines exit the plate 500 at its ends 502 and 504, essentially as illustrated in FIG. 3. Few or none of the magnetic field lines exit the plate 500 through its top, bottom or sides.

Figure 7:
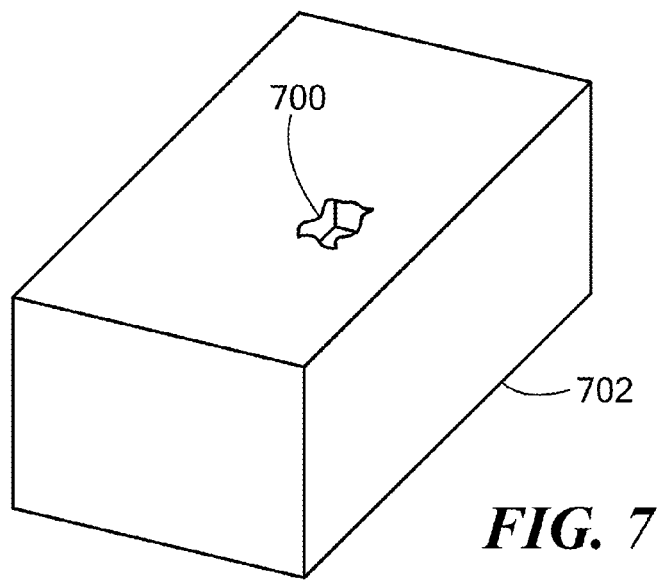
FIG. 7 schematically illustrates the plate of FIG. 5 with a defect in its surface.

However, if the plate suffered a defect, some material is lost, as exemplified in FIG. 7 by a defect 700 in the surface of a block 702. Consequently, one or more of the small magnetic dipoles, such as magnetic dipoles 602 or 604, is lost, and the resulting asymmetric arrangement of the remaining magnetic dipoles results in some magnetic field lines exiting the block through the top, bottom and/or sides of the block 702. Accordingly, a signature of a defect, i.e., a missing volume of ferromagnetic material, may be thought of as being approximated by an equal volume of oppositely-oriented magnetic dipoles. Even if only interior, i.e., non-surface, magnetic dipoles are lost, the resulting asymmetric arrangement of the remaining magnetic dipoles results in some magnetic field lines exiting the block through the top, bottom and/or sides of the block 702.

The local magnetic field in the vicinity of the lost magnetic dipoles is similar to the magnetic field described above, with respect to FIGS. 3 and 4. Consequently, the location of the defect can be found by locating a portion of the magnetic field produced by the plate 702 that has a shape similar to the shape of the Bx or By graph in FIG. 4. Thus, the general shapes of the Bx and By graphs may be used as magnetic signatures of defects.

Pipe Defect Detection

Figure 8:
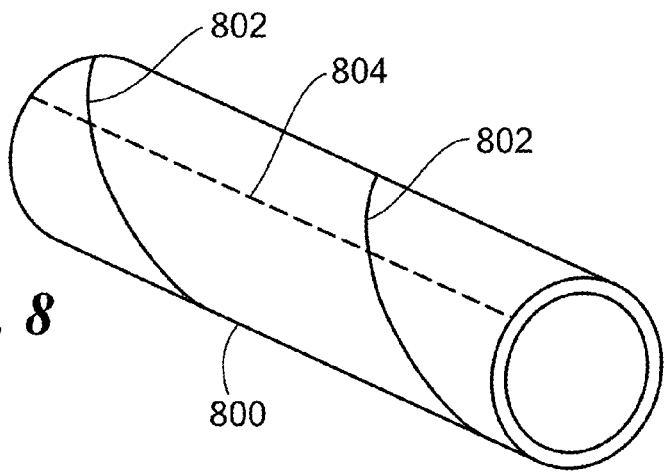
FIG. 8 schematically illustrates a hypothetical pipe, showing a helical thickness artifact from its manufacture, as known in the prior art.
Figure 9:
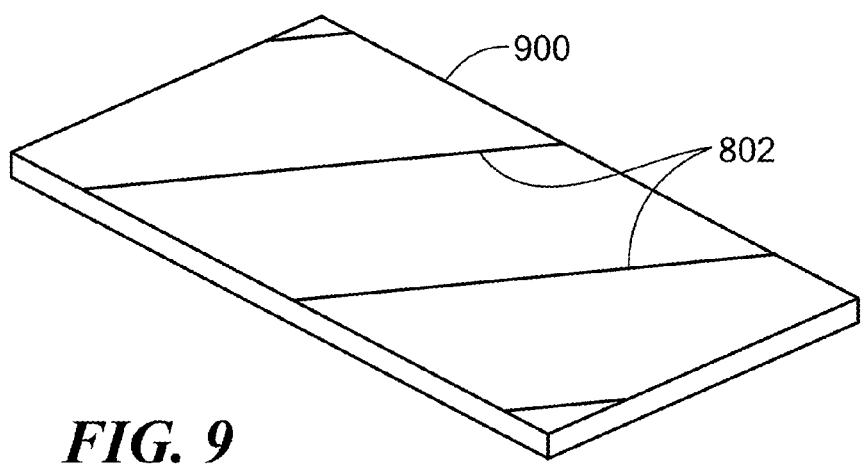
FIG. 9 schematically illustrates the pipe of FIG. 8 after being conceptually cut and unrolled, as known in the prior art.

Pipe is fabricated in a variety of ways. Each method leaves behind inhomogeneous features, either in composition, thickness, temperature history or some other artifact. All of these have the potential to cause the item's intrinsic, residual magnetic field to not be smooth, but to have features of size and complexity such that finding the defect's signature is not straight forward. A common manufacturing artifact in pipes is a spiral (helical) pattern of thickness down the length of the pipe. FIG. 8 schematically illustrates a pipe 800, showing such a helical thickness artifact 802 from its manufacture. Conceptually, the pipe 800 can be cut along a line 804 parallel to its longitudinal axis and then unrolled into a flat plate 900, as schematically illustrated in FIG. 9. This plate 900 may be analyzed, as described above, with respect to FIGS. 3-7.

Figure 10:
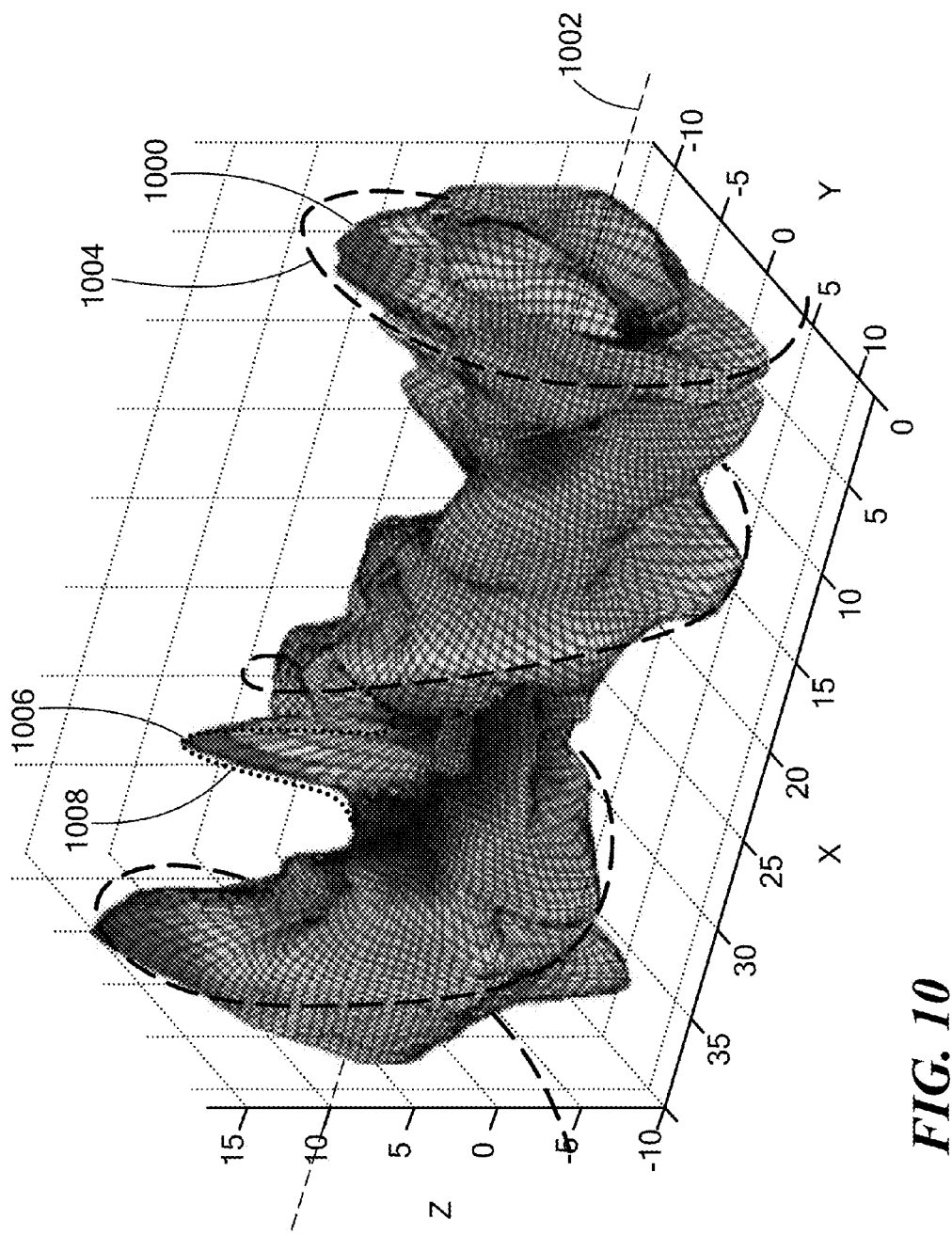
FIG. 10 contains a graph of one component of a magnetic field about an actual pipe having a defect in its external surface, according to an embodiment of the present invention.

FIG. 10 contains a graph of the x component of the magnetic field about an actual 4.5 inch (114.3 mm) diameter pipe having a 1 inch×1 inch×0.06 inch (25.4 mm×25.4 mm×1.5 mm) defect in its external surface. The graph is presented as a distorted surface 1000. Radial distance of the surface 1000 from a longitudinal axis 1002 of the pipe indicates strength of the x component of the magnetic field.

The manufacturing processes of the pipe leaves behind artifacts in the magnetic field. The often-observed helical pattern in the field due to manufacturing processes, feature 802 (FIGS. 8 and 9) is evident in FIG. 10, where a ridge of magnetic field strength spatially corresponds to the helical manufacturing feature, as indicated by dashed helical line 1004.

Also evident in FIG. 10 is a peak 1006 in magnetic field strength. Furthermore, as indicated by dotted line 1008, the shape of the surface proximate the peak 1006 is similar to the shape of the By curve in FIG. 4 and is, therefore, characteristic of a defect.

Similar analyses may be performed using the y component of the magnetic field about the pipe and the z component of the magnetic field. Correlating locations of defects found by the three analyses provides the location of the defects more accurately than the analysis of only one component of the magnetic field.

Sensor Array

Figure 11:
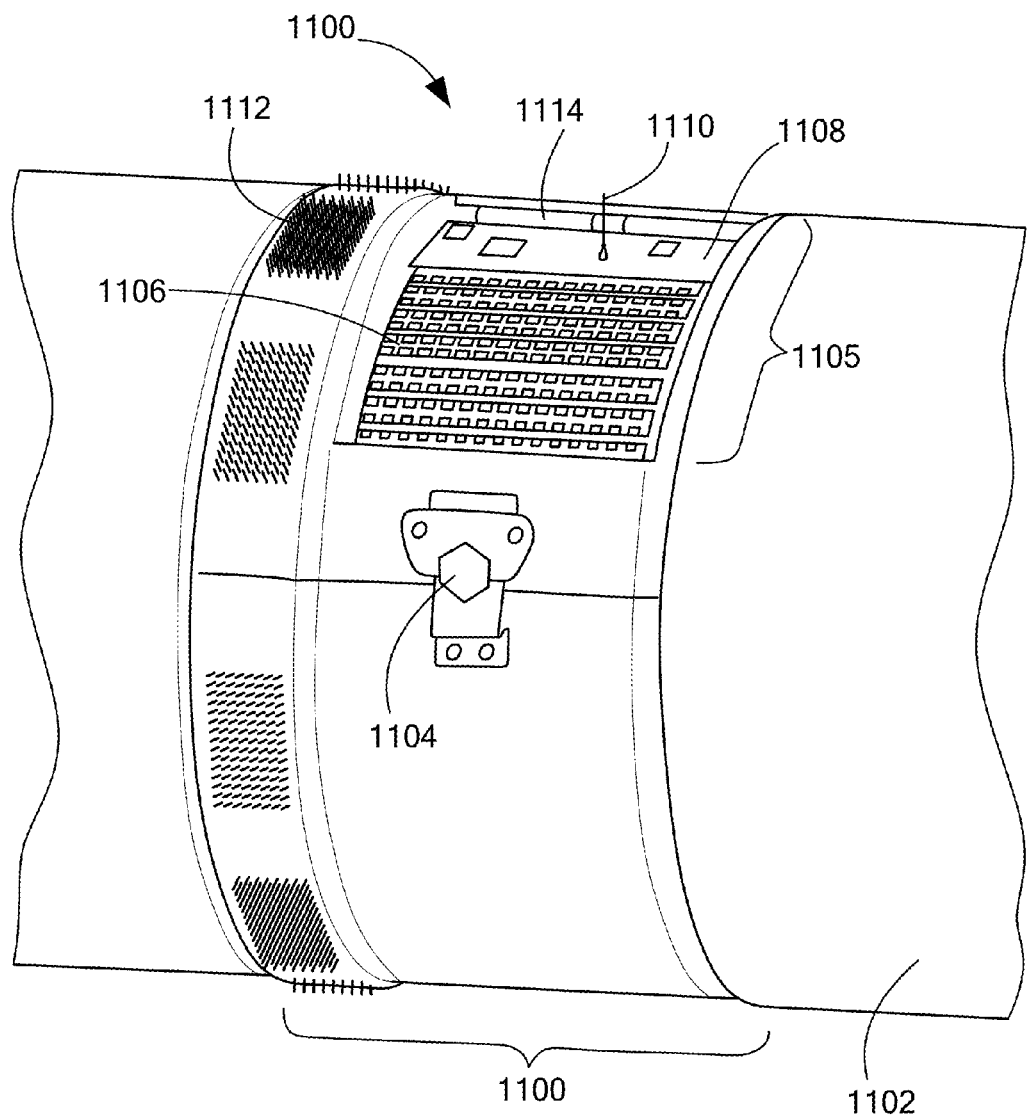
FIG. 11 is a side view of a magnetometric sensor unit, according to an embodiment of the present invention.

FIG. 11 schematically illustrates one embodiment of the present invention. In this embodiment, a magnetometric sensor unit 1100 is strapped around a pipe 1102. The magnetometric sensor unit 1100 includes two semicircular portions (half shells) that are hinged together. The hinge is located on the back side of the magnetometric sensor unit 1100 and thus is not visible in FIG. 11. A releasable latch 1104 mechanically secures the two half shells to each other, thereby clamping the magnetometric sensor unit 1100 around the pipe 1102. The latch 1104 secures the magnetometric sensor unit 1100 to the pipe 1102 sufficiently tightly to prevent rotation of the magnetometric sensor unit 1100 around the pipe 1102 or translation of the magnetometric sensor unit 1100 along the pipe 1102, in response to forces expected to be encountered in normal use, such as in an industrial installation. The latch 1104 may be keyed, to prevent unauthorized removal or tampering with the magnetometric sensor unit 1100. The magnetometric sensor unit 1100 may be constructed so as to meet ATEX/UL directive standards regarding explosion protection, as well as being weatherproof.

Advantageously, since the magnetometric sensor unit 1100 does not need to be in contact with the item being measured, it may be attached to the pipe 1102 over any existing pipe covering, such as thermal insulation or pipe surface treatment, without removing the pipe covering. Additional thermal insulation or other covering may be applied over an installed magnetometric sensor unit 1100, if desired.

A portion 1105 of the outer housing of the magnetometric sensor unit 1100 is shown removed in FIG. 11 to reveal an array 1106 of magnetometric sensors. Each magnetometric sensor in the array 1106 may be a three-axis magnetometric. As can be seen through the opening 1105 in outer housing, the magnetometric sensors 1106 are disposed around the pipe 1102 in rings. Each ring includes a number of magnetometric sensors spaced regularly around the ring. These internal rings are spaced apart longitudinally along the pipe 1102 at regular intervals, essentially creating a regular two-dimensional array of magnetometric sensors disposed parallel to the outer surface of the pipe 1102 and spaced a fixed distance, possibly zero, from the pipe 1102. A core circuit board 1108 includes an antenna 1110 and circuits that control the magnetometric sensors 1106, collect data from the magnetometric sensors 1106 and communicate with other magnetometric sensor units and/or a base station (not shown) via a wireless communication network.

A set of energy harvesters 1112 generates electricity from a temperature difference between the pipe 1102 and the ambient environment. Optionally or alternatively, the energy harvesters 1112 may include photovoltaic cells and/or any other suitable energy harvesting technology. Optionally or alternatively, a primary battery, with or without an energy harvester, may be used, if the power needs and lifetime are such that this is a viable alternative. Rechargeable batteries 1114 may be included to store harvested energy until it is needed by the core circuit board 1108. The energy harvesters 1112 may be arranged in a ring, as shown.

Spacing of the magnetometers 1106 may be selected to achieve a desired magnetometer density, such as about a 0.3 inch (7.6 mm) inter-magnetometer spacing, i.e., spacing between adjacent three-axis magnetometer sensors. The inter-magnetometer spacing may be selected based on the minimum size defect to be detected. The inter-magnetometer spacing should be selected such that the smallest defect to be detected is spanned by a sufficient number of three-axis magnetometer sensors so as to be able to detect the shape of the defect's signature in the magnetic field map.

Figure 12:
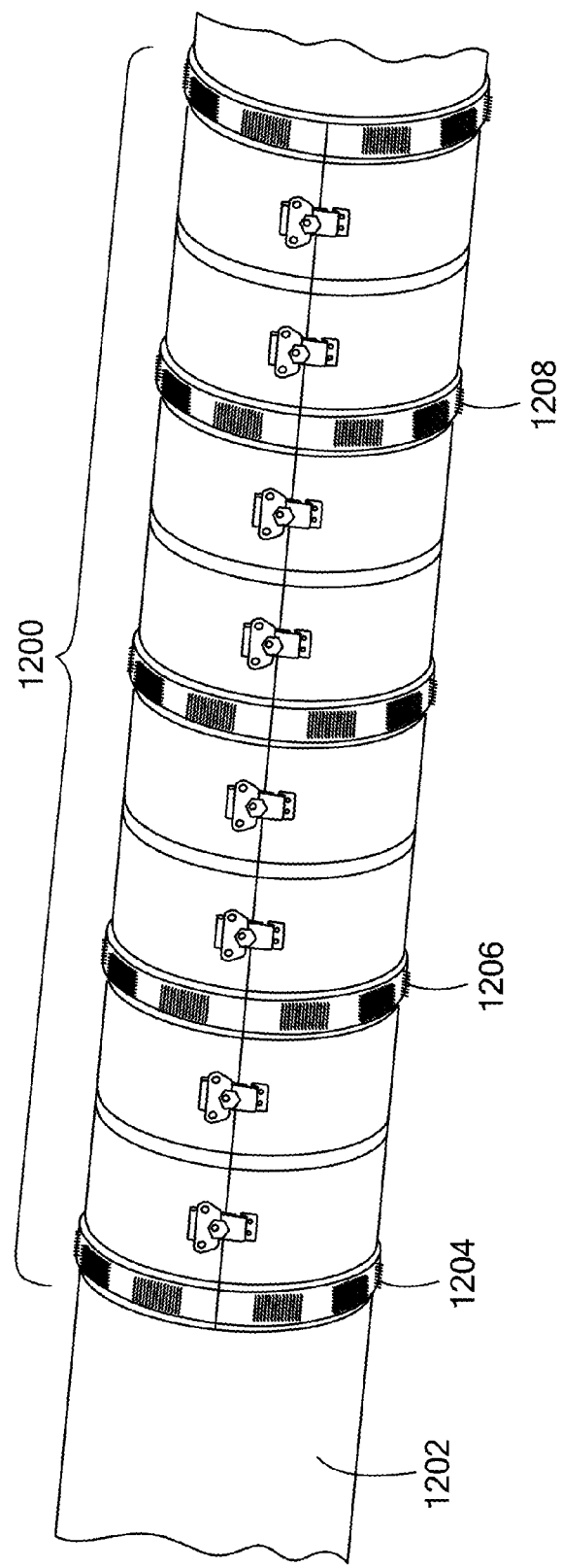
FIG. 12 schematically illustrates a set of magnetometric sensor units attached to a pipe, according to an embodiment of the present invention.
Figure 13:
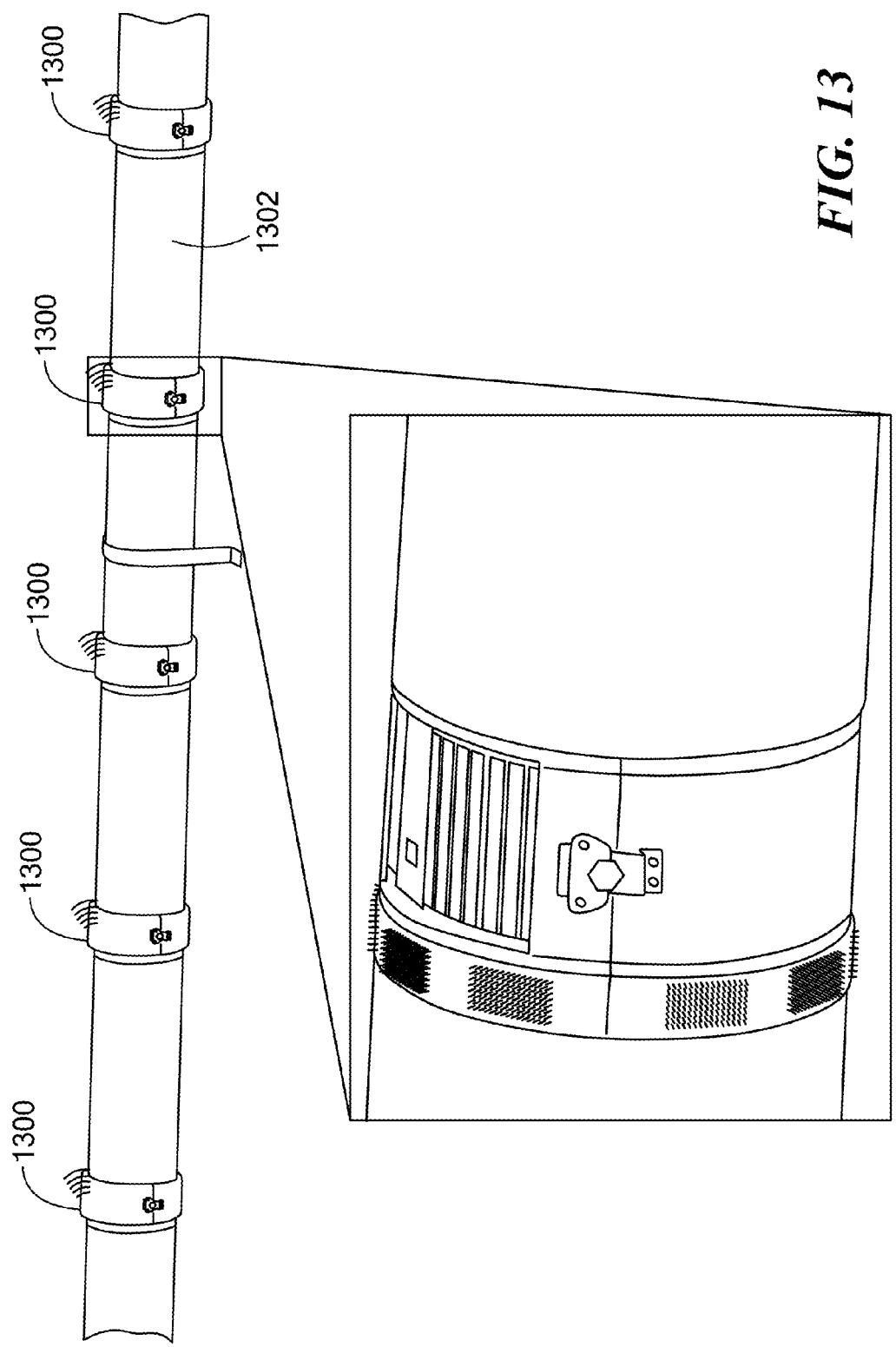
FIG. 13 schematically illustrates a set of magnetometric sensor units attached to a pipe, according to an embodiment of the present invention.

FIG. 12 schematically illustrates a set of magnetometric sensor units 1200 attached to a pipe 1102. As shown in FIG. 12, several magnetometric sensor units 1200 may be tightly packed along all or a portion of the length of the pipe 1202. In this embodiment, each energy harvester ring, exemplified by energy harvester rings 1204, 1206 and 1206, powers two magnetometric sensor units, one on each side of the energy harvester ring. As schematically shown in FIG. 13, a set of magnetometric sensor units 1300 may be attached to a pipe 1302 and spaced apart from each other along the pipe 1302.

Figure 14:
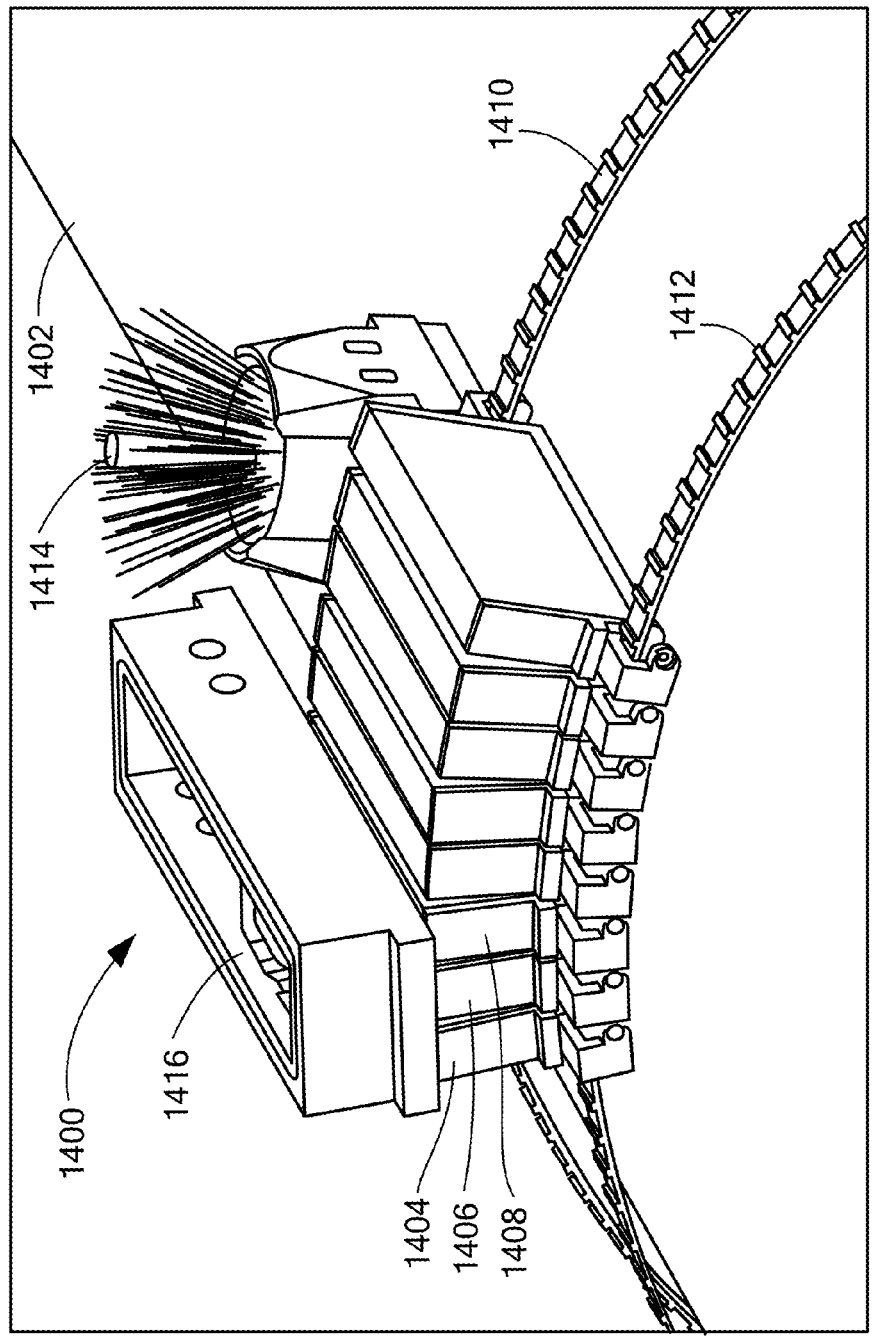
FIG. 14 is a perspective schematic view of an array of magnetometric sensors disposed circumferentially around a pipe, according to an embodiment of the present invention.

FIG. 14 is a close-up view of a magnetometric sensor array 1400, according to another embodiment. In this embodiment, the array of magnetometric sensors 1400 is disposed circumferentially or part way around a pipe 1402, as in FIGS. 11-13. The array 1400 includes several array modules, exemplified by array modules 1404, 1406 and 1408. However for clarity, only eight array modules are shown in FIG. 14. Each array module 1404-1408 may be detachably attached to a pair of circumferential mounting rings 1410 and 1412. Optionally or alternatively, the array of modules 1404-1408 may be packaged inside a protective housing, as discussed with respect to FIGS. 11-13. In some embodiments, additional array modules are attached to the mounting rings 1410 and 1412, so the pipe 1402 is encircled by array modules. However, in other embodiments, array modules 1404-1408 may cover only a portion of the circumference of the pipe 1402. In some embodiments, the array modules 1404-1408 may be attached via detachable electric plugs that facilitate field replacement of the array modules 1404-1408. In some embodiments, the array modules 1404-1408 are hot swappable.

The array 1400 may be powered by an energy harvester 1414 and may include a core circuit board 1416. The array 1400 includes a wireless transceiver and antenna (not shown).

Figure 15:
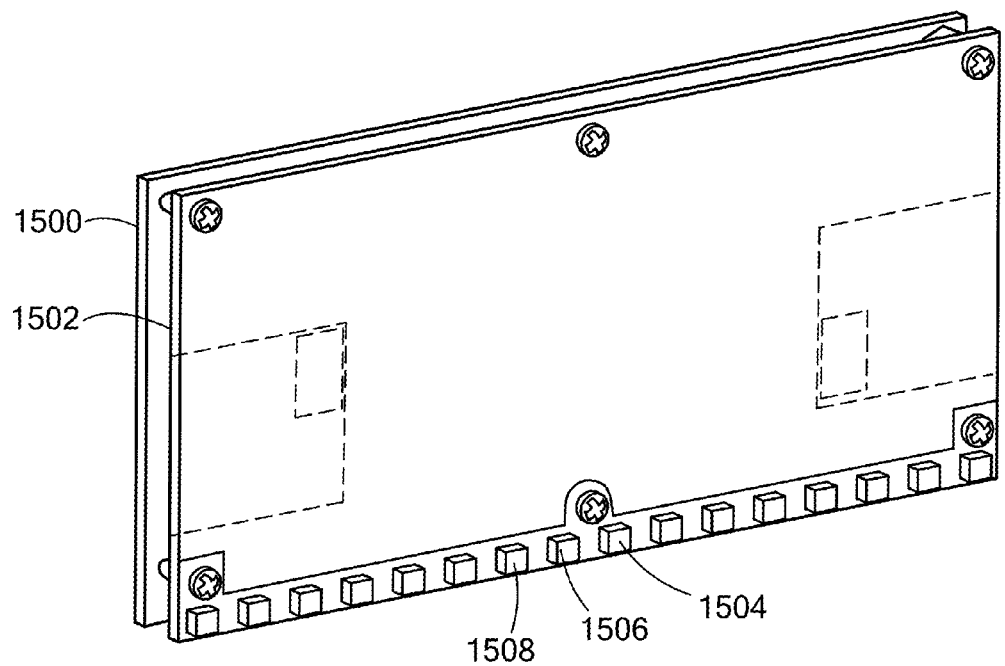
FIG. 15 is a perspective schematic view of a pair of circuit boards, bearing magnetometers, such as in each element of the array of magnetometric sensors of FIG. 14, according to an embodiment of the present invention.

In some embodiments, each array module 1404-1408 includes a pair of circuit boards 1500 and 1502, as shown in FIG. 15. Each circuit board of the pair of circuit boards 1500-1502 includes a row of three-axis magnetometers, exemplified by magnetometers 1504, 1506 and 1508. In some embodiments, each circuit board includes 16 three-axis magnetometers 1504-1508.

Each magnetometric sensor 1504-1508 inside the array module 1500-1502 includes three magnetometers (equivalently a three-axis magnetometer sensor). The three magnetometers may be mutually orthogonally oriented, or they may be oriented according to some other known arrangement. Magnetometer orientation here refers to the axis of primary sensitivity of the magnetometer. In some embodiments, each array module 1404-1408 (FIG. 14) includes an array, such as a 16×1 array (as in FIG. 15) or a 16×16 array, of three-axis magnetometer sensors.

Pattern Matching to Locate Signatures of Defects

Figure 16:
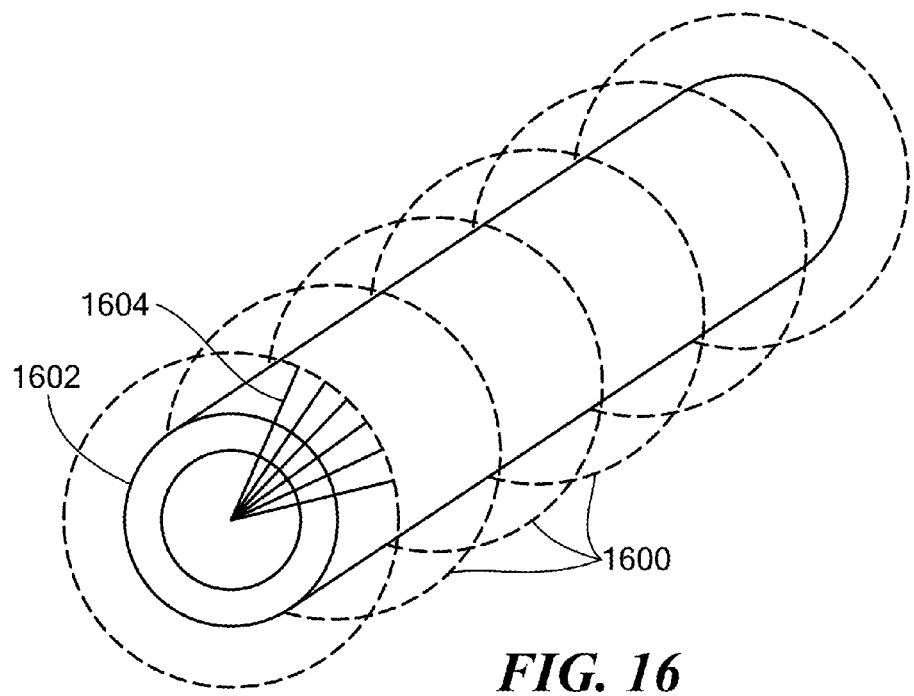
FIG. 16 is a perspective schematic view of rings of magnetometric sensors disposed about a pipe, according to an embodiment of the present invention FIGS. 17 and 18 include graphs of magnetometric data along two respective dimensions of an actual pipe, according to an embodiment of the present invention.

As noted, in some embodiments, magnetometric data is searched for any of several predefined spatial patterns (signatures) that indicate a defect. The patterns may be sinusoidal, and the length (wavelength) of the sinusoid may be proportional to the size of the defect. In this sense, the wavelengths of the sinusoids are generally unknown a priori. As described above, rings 1600 of magnetometric sensors are disposed around the circumference of a pipe 1602 to creating a regular two-dimensional array of magnetometric sensors disposed parallel to the outer surface of the pipe 1602, as schematically illustrated in FIG. 16. This array of magnetometric sensors produces magnetometric data. FIG.

Figure 17:
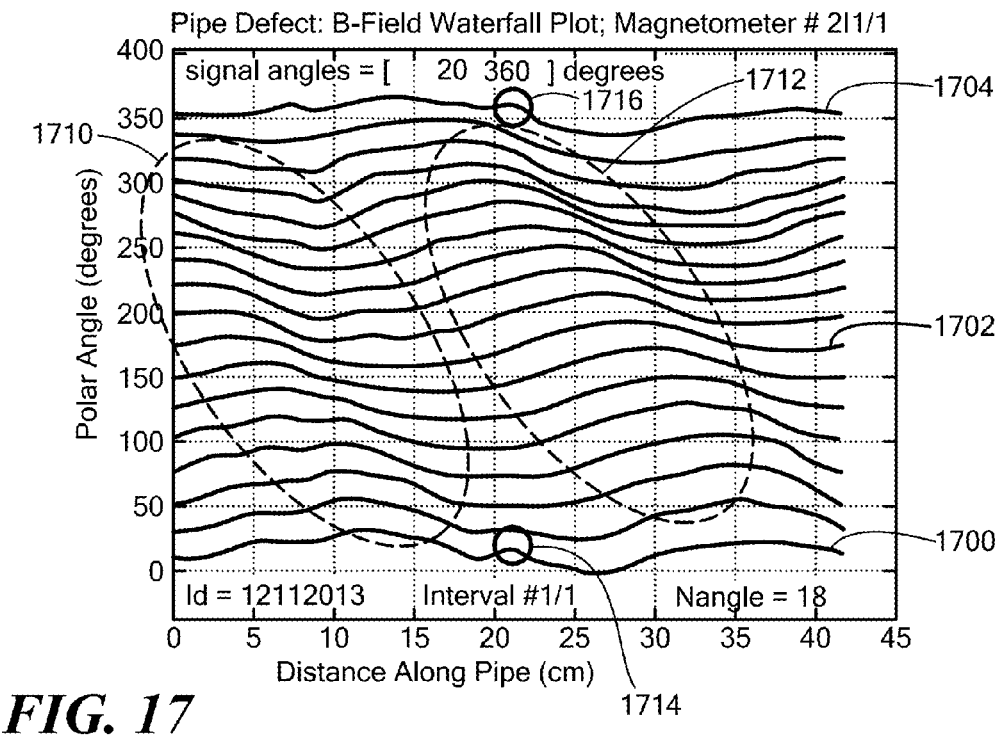
Figure 18:
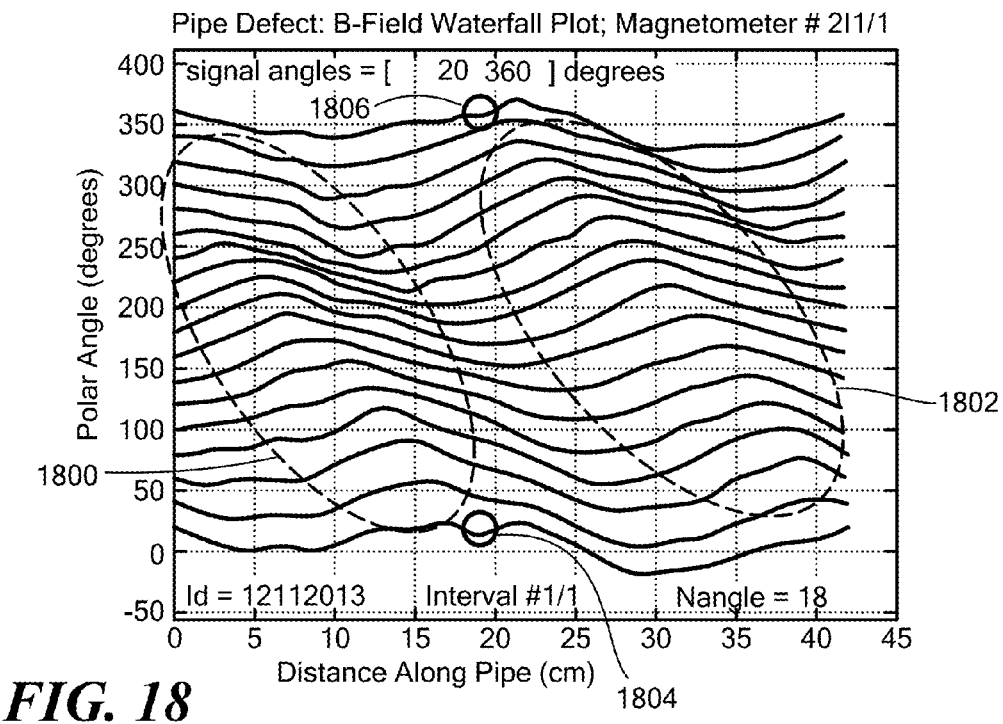

17 includes a graph of such magnetometric data from an actual pipe. The data in FIG. 17 plots component magnetic field strengths detected by x-oriented magnetometers, i.e., along the length of the pipe. FIG. 18 plots component magnetic field strengths detected by z-oriented magnetometers, i.e., normal (or nearly normal) to the surface of the pipe. A graph (not shown) plots component magnetic field strengths detected by y-oriented magnetometers, i.e., perpendicular to the x-oriented and y-oriented magnetometers.

Each magnetometric sensor (within a sensor unit 1100) (FIG. 11) is disposed at a given angular position ("clock position"), exemplified at 1604 (FIG. 16), around the ring 1600. In the embodiment that generated the data for FIGS. 17 and 18, each ring includes 18 magnetometric sensors. However, other numbers of sensors may be used. Each generally horizontal line, exemplified by lines 1700, 1702 and 1704, represents data from the x-component sensing magnetometer at a discrete angular position around the pipe. Thus, the vertical axis represents angular position around the pipe. The horizontal axis represents distance along the length of the pipe. Thus, points along each line 1700-1704 represent magnetic field strengths along the length of the pipe. Similarly, FIG. 18 shows the z-component of the magnetic field in positions collocated with the data in FIG. 17. Helical variations in the magnetic field due to pipe manufacturing processes are evident, as indicated at 1710, 1712, 1800 and 1802. Signatures of a defect are present at 1714, 1716, 1804 and 1806. How this defect is detected is described below.

Data collected from the magnetometers needs to be processed so that it is continuously differentiable in the spatial dimensions along the pipe and around the pipe. Standard approaches are used to fill in gaps in the sensor data and smooth and interpolate the data, such that spatial partial derivatives can be calculated.

Figure 19:
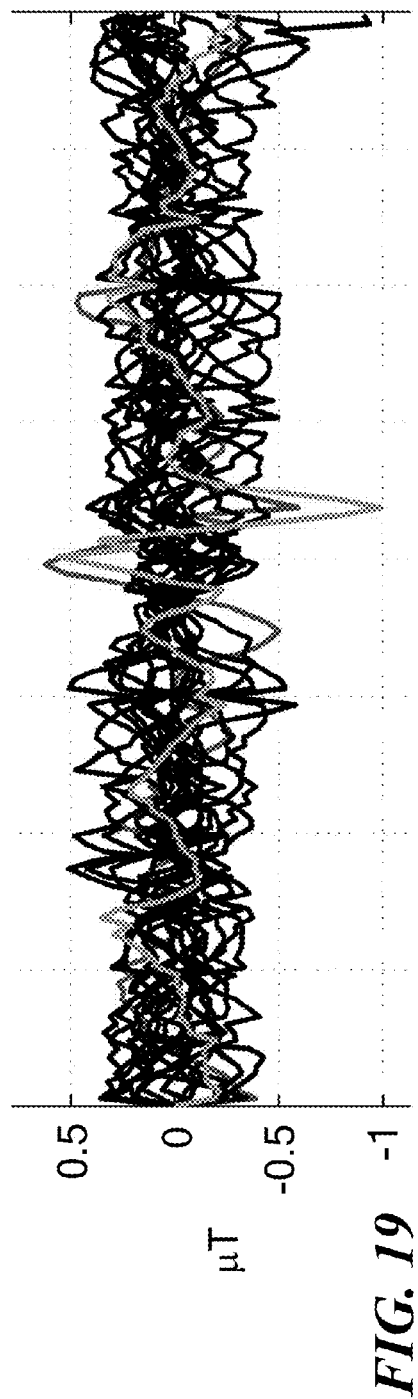
FIGS. 19 and 20 contain plots of derivatives calculated from the plots of FIGS. 17 and 18, respectively, according to an embodiment of the present invention.
Figure 20:
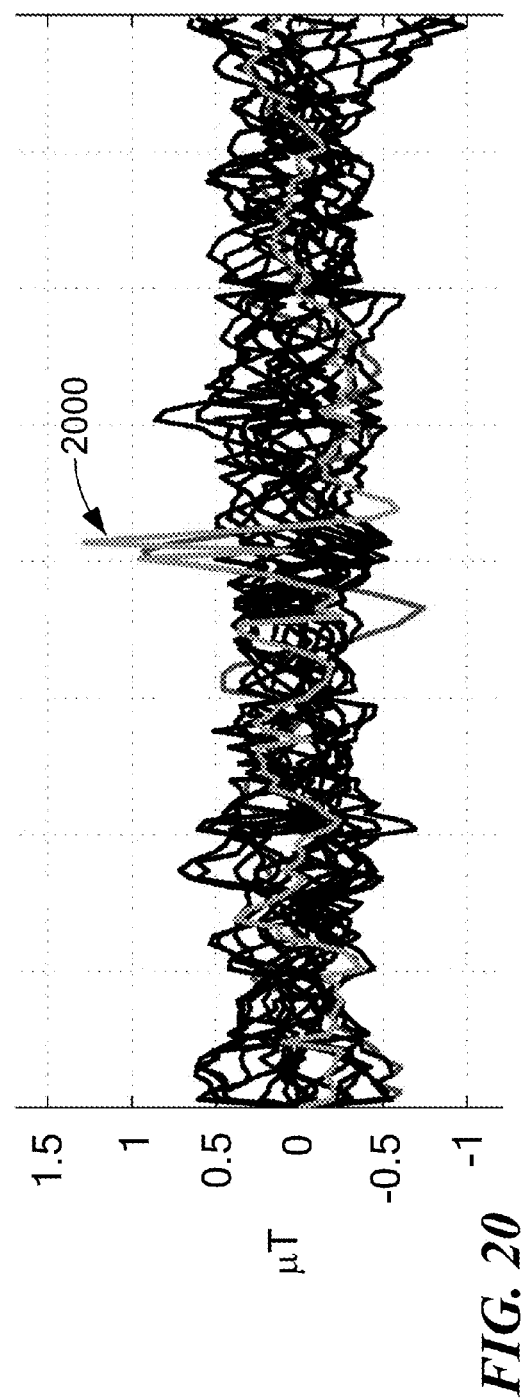

Along each line 1700-1704 in the plot of FIG. 17, and similarly along each line in the other two component directions (such as FIG. 18, which shows one more of the vector components of the magnetic field), spatial derivatives (slopes or rates-of-change) are calculated. FIGS. 19 and 20 are plots of the derivatives calculated from FIGS. 17 and 18, respectively. The motivation for calculating derivatives is that, while the magnetic signature of the defect and the residual magnetic field are similar in magnitude, the defects tend to be of smaller extent and have steeper rises and falls. Hence, a derivative tends to amplify this higher-frequency behavior, and the defect stands out in both amplitude and wavelength, as compared to the features of the derivative of the residual field. As can be seen in FIG. 20, for example, most of the traces have a moderate amplitude (hence, moderate slopes in the magnetic field signal). These are the traces that are in non-defect areas. The light grey traces 2000 at the center of FIG. 20 are the two traces that cross the defect. It is seen that in this derivative plot, these traces stand out in magnitude from the non-defect (residual) areas, providing additional information for a detection algorithm to operate on.

An automatic pattern matcher searches the resulting derivatives for portions that match one of several sine or cosine templates. Each template corresponds to a different spatial wavelength. Many templates are used, because, as noted, the spatial extent of the defect, hence the spatial wavelength of the defect's sine and cosine, are not known a priori. The template with the wavelength that has the strongest correlation to the magnetic field data is used for detection and characterization of the defect.

The locations of defects ascertained in the three separate analyses, i.e., for the x, y and z components of the magnetic field, are merged to yield a final defect location and confidence level.

Defect Characterization

Once the location of a defect has been found, the defect may be characterized in terms of volume (amount of material lost) and surface extent (at the surface of the pipe or parallel to the surface of the pipe if the defect is internal to the pipe). In some cases, assumptions are made about the general shape of a defect. For example, the defect may be assumed to be generally circular or elliptical on a surface of a pipe or have a vertical profile of some sort. With these sorts of assumptions, the area and depth of the defect can be approximated.

Figure 21:
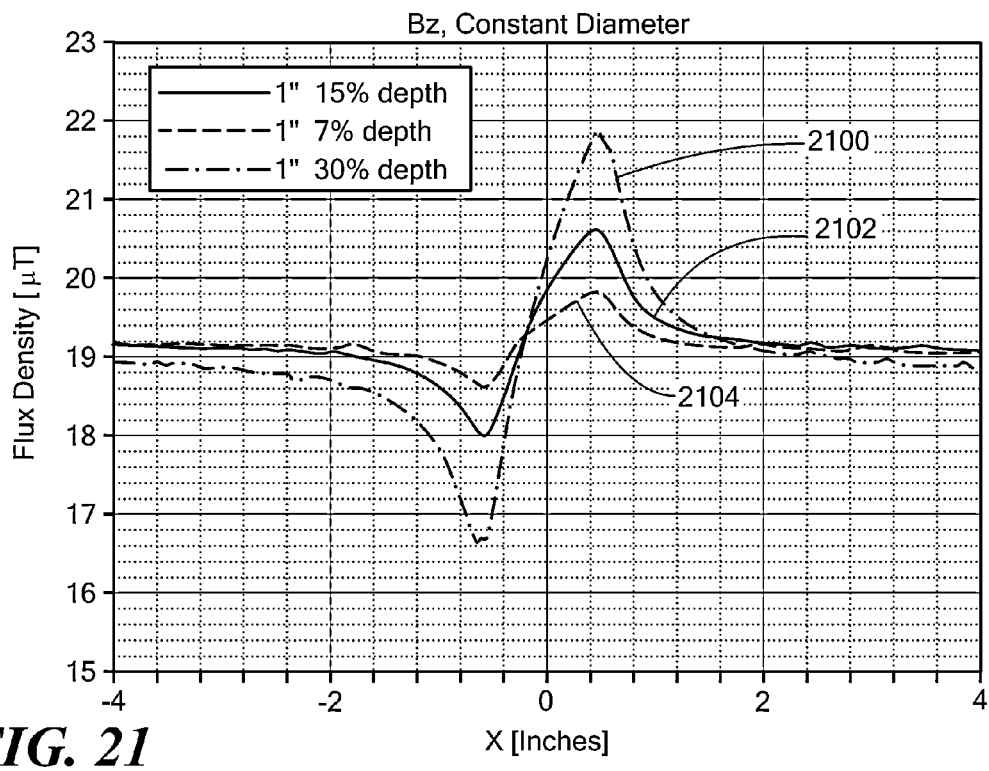
FIG. 21 is a graph of magnetic field strength for three simulated defects, all of the same diameter, but of different depths, according to an embodiment of the present invention.
Figure 22:
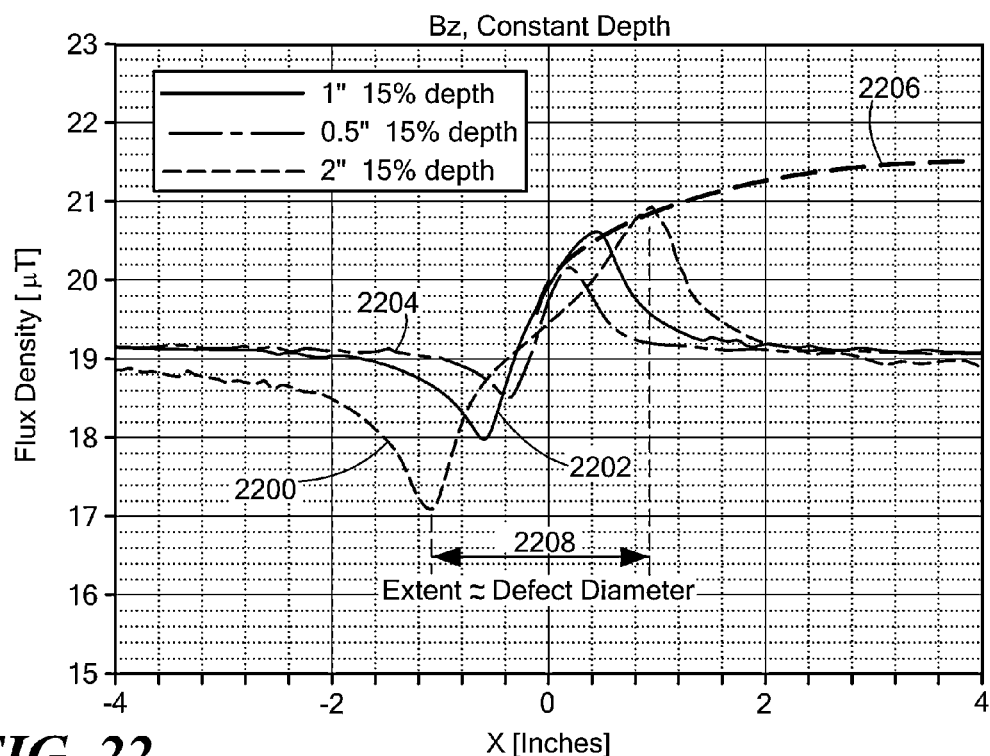
FIG. 22 is a graph of magnetic field strength for three simulated defects, all having the same depth, but of different diameters, according to an embodiment of the present invention.

The z component of the measured magnetic field is normal to the surface of the ferromagnetic material being measured, as shown in FIG. 21 for a pipe. The amplitude of the z component of the magnetic field is proportional to the amount of ferromagnetic material lost due to the defect. Thus, for defects having identical diameters, the z component of the magnetic field is also proportional to depth of the defect. The graph in FIG. 21 represents three simulated defects, all of the same diameter at the surface of the pipe (four times the wall thickness of a pipe). Curve 2100 represents a defect whose depth is 30% of the wall thickness of the pipe. Curve 2102 represents a defect whose depth is 15% of the wall thickness of the pipe. Curve 2104 represents a defect whose depth is 7% of the wall thickness of the pipe. As can be seen from the graph, the amplitude of the z component of the magnetic field is related to the depth of the defect. The amplitude of the z component is more proportional to the volume of the material missed, and for a set of assumptions on typical shapes of defect growth, the depth of the defect can be inferred. This result can be seen in all three magnetic field axes. Thus, given a magnetic field component amplitude, the volume of the defect can be determined, presuming the magnetization of the material in known, as further described below. This information, combined with a defect area and depth profile, allow the determination of an approximate defect depth, However, for a given defect depth, the amplitude of any of the components of the magnetic field increases with an increase in the surface area of the defect. This is to be expected, in that the amplitude of the signal is proportional to the volume of the defect, and as surface area increases for a specified depth, the volume of the defect also increases. In FIG. 22, the graph represents the z-component of the magnetic field for three simulated defects, all having the same depth (15% of the wall thickness of the pipe). Curve 2200 represents a defect whose diameter is 2 inches (50.8 mm). Curve 2202 represents a defect whose diameter is 1 inch (25.4 mm). Curve 2204 represents a defect whose diameter is 0.5 inch (12.7 mm). As can be seen, with a constant defect depth, the amplitude of the z component of the magnetic field increases with the surface area of a defect, due to the defect's volume increasing. However, the increase follows a predictable curve (since it represents volume), shown at 2206. Consequently, this increase can be accounted for in a mathematical model. The distance from the valley in the graph to the peak in the graph, indicated as "extent" 2208, is proportional to the extent of the defect along the direction of the magnetometers that created the plot.

The strengths of the defect signals are proportional to both the amount of material missing and the magnetization level of the material. Thus, determining a pipe's magnetization is useful to determining the volume of the material missing, and thus is useful to characterizations of area and depth of the defect. The determination of the magnetic field should not be done at the defect site, but should be done in a nearby, non-defect site. This measure of local "residual" pipe magnetization enables normalizing defect signals, thereby effectively calibrating the defect volume and depth calculations. Having located the defects, as described above, a defect detection system measures the pipe's residual magnetization level, i.e., its magnetization level in an area that does not include a defect.

Figure 23:
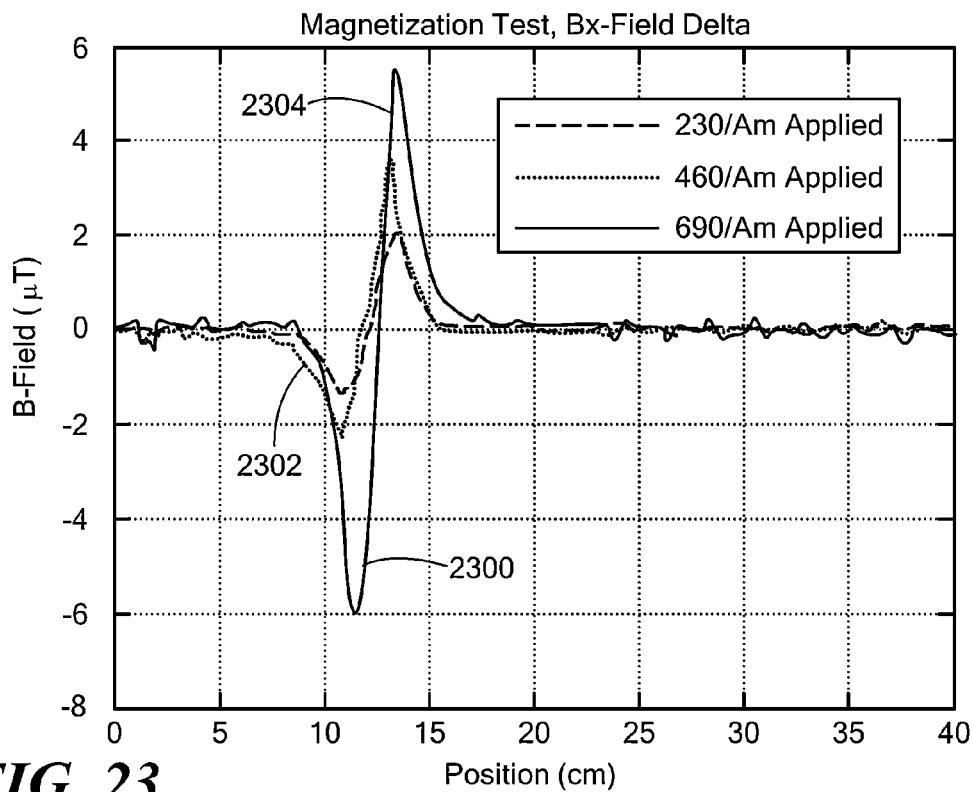
FIG. 23 is a graph of magnetic field strength along an x axis proximate a defect in a pipe, according to an embodiment of the present invention.

FIG. 23 is a graph of magnetic field strength along the x axis (longitudinal down the pipe) proximate a defect in a pipe. All three plots represent the same pipe defect, and all three plots show the signature of a defect. However, before data for each plot was collected, the pipe was magnetized to a different degree. For plot 2300, the pipe was magnetized with a coil operated at a strength of 690 A/m (amps/meter). For plot 2302, the pipe was magnetized at 460 A/m. For plot 2304, the pipe was magnetized at 230 A/m. As can be seen from the plots, defect signals increase in direct proportion to a pipe's magnetization.

Figure 24:
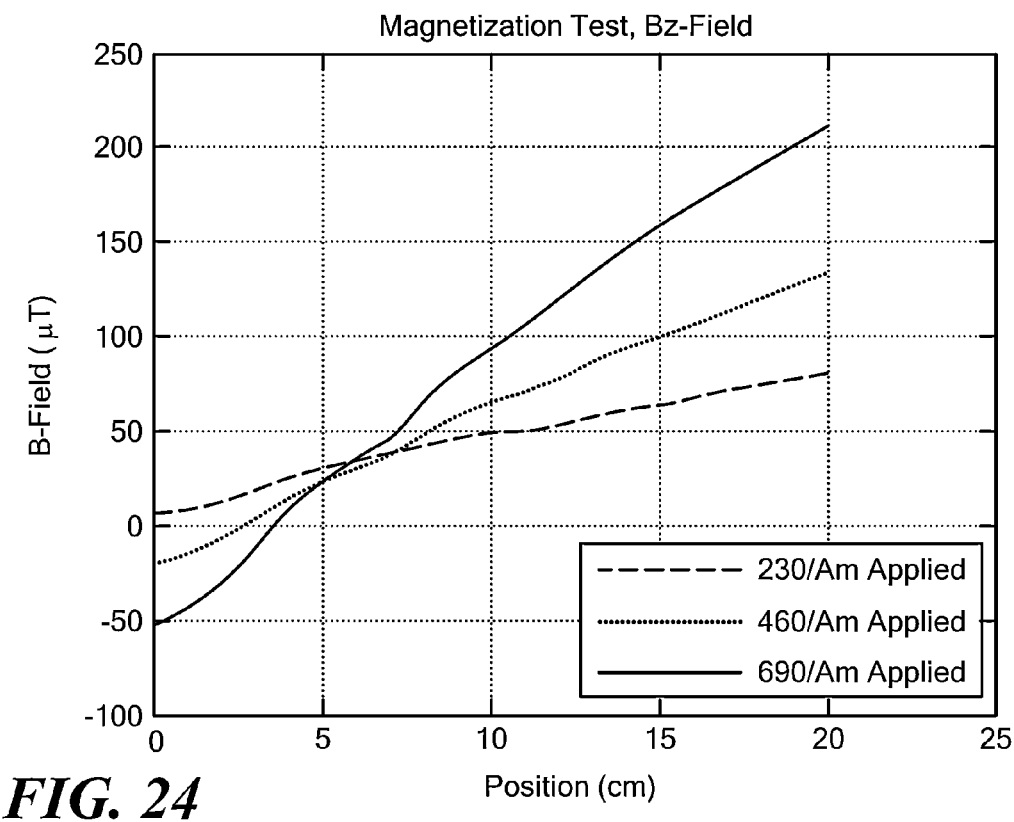
FIG. 24 is a graph of magnetic field strength along an z axis proximate a defect in a pipe, according to an embodiment of the present invention.

One embodiment for measuring the strength of the local, residual field in the pipe is shown graphically in FIG. 24. For pipes that have leakage paths (often due to them being inhomogeneous due to manufacturing processes), the z magnetic field (radial with respect to the pipe's central axis) has a slope down the length of the pipe. This slope is proportional to the magnetic field strength. The sloped traces in FIG. 24 correspond to the magnetization cases shown in FIG. 23, with the smallest slope corresponding to the 230 A/m case and the largest slope corresponding to the 690 A/m case. Under these conditions, the z-component of the magnetic field provides an independent measure of the residual magnetic field strength in the pipe.

Figure 25:
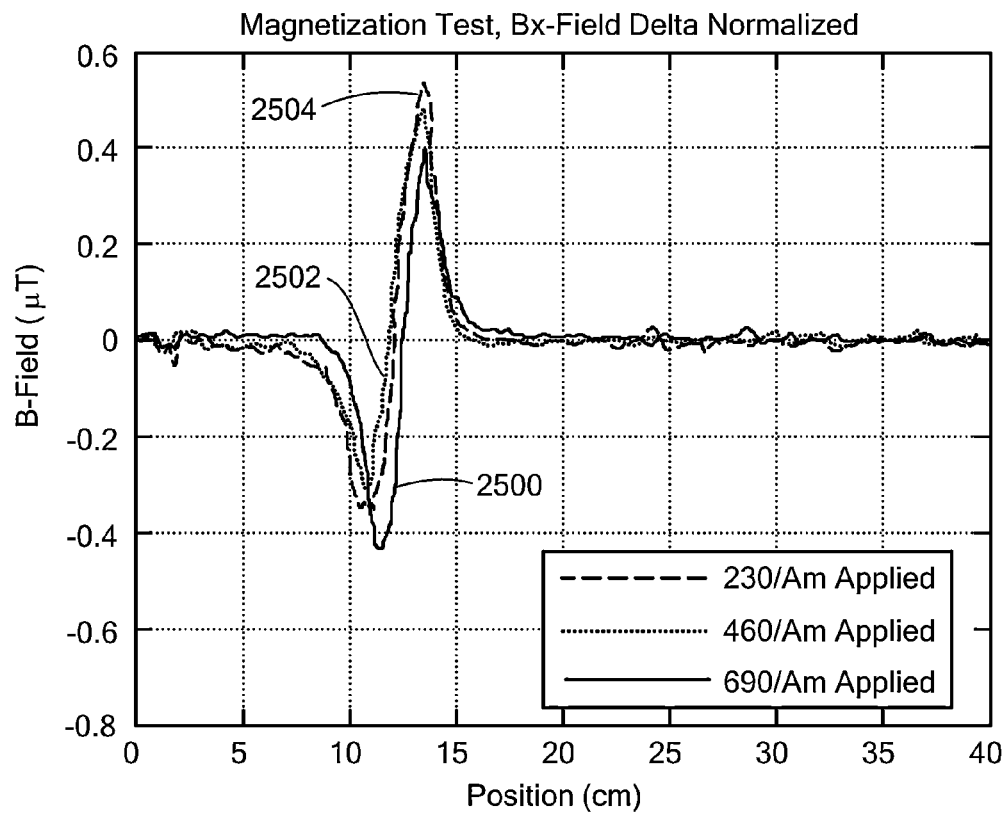
FIG. 25 is a graph of the magnetic field strength of FIG. 23, after normalization, according to an embodiment of the present invention.

The plots of FIG. 23 have been normalized, according to the residual magnetization level, yielding plots in FIG. 25, which are numbered to correspond with the plots in FIG. 23. As can be seen by comparing FIGS. 23 and 25, signal amplitude can be made largely independent of pipe magnetization level by normalizing according to the pipe's residual magnetization level. In this way magnetic measurement amplitudes can be converted to volume and area, with a calculation of depth following.

Other methods of determining the residual magnetization level of a pipe are envisioned. For example, a pipe may be magnetized to a known level when the pipe is installed, or the pipe may be magnetized to an arbitrary level and the magnetization level may be measured. In either case, this magnetization level may be stored in a memory accessible by a base station and used later, when defects have been detected and volume and depth information is desired. Optionally or alternatively, even if information about a pipe's previous magnetization level is not stored, once defects have been detected, the magnetometric sensors may be used to measure a pipe's residual magnetization in one or more areas away from all detected defects using the slope method, above, or other independent measurement approaches.

Figure 26:
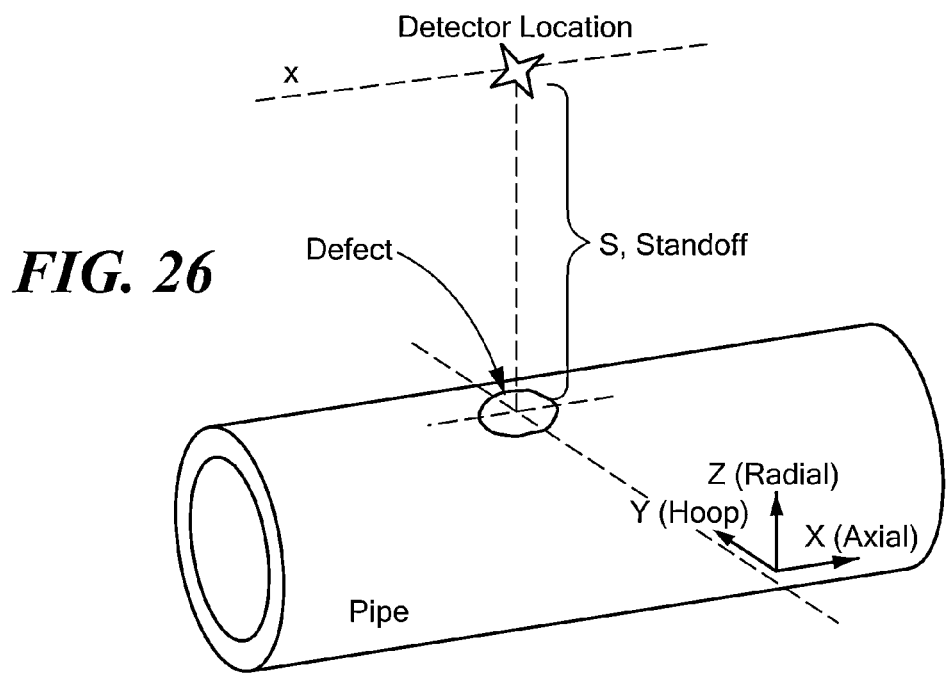
FIG. 26 is a perspective schematic illustration of a pipe and standoff between a detector and a defect in the pipe, according to an embodiment of the present invention.

As used herein, "standoff" means distance between a defect and a magnetometer, as schematically illustrated in FIG. 26. Theory and tests show that signal strength falls off according to an inverse square law when close to a magnetic dipole. If the sensor has a standoff similar in distance to the characteristic length of the dipole, the dipole appears as two independent poles, and the signal strength falls of as an inverse square. As the standoff increases, the extent of the dipole appears to diminish and becomes a point source. Under these conditions, theory and test shows that the signal strength falls off according to an inverse cube law. Thus, small defects have more signal loss as the standoff moves beyond the size of the defect, while a large defect continue to "enjoy" an inverse square degradation of its signal for larger standoffs. For example, for a 1 inch (25.4 mm) square defect, signal loss is greater than about an order of magnitude, when standoff is increased from 0.25 inch (6.4 mm) to 2.25 inches (51.2 mm). The residual pipe magnetization features fall off in strength slower due their larger spatial extent. Nevertheless, the apparatus and methods described herein reliably detect defects expected to be found in conventional pipe, such as those in oil and gas pipelines, refineries, etc.

Figure 27:
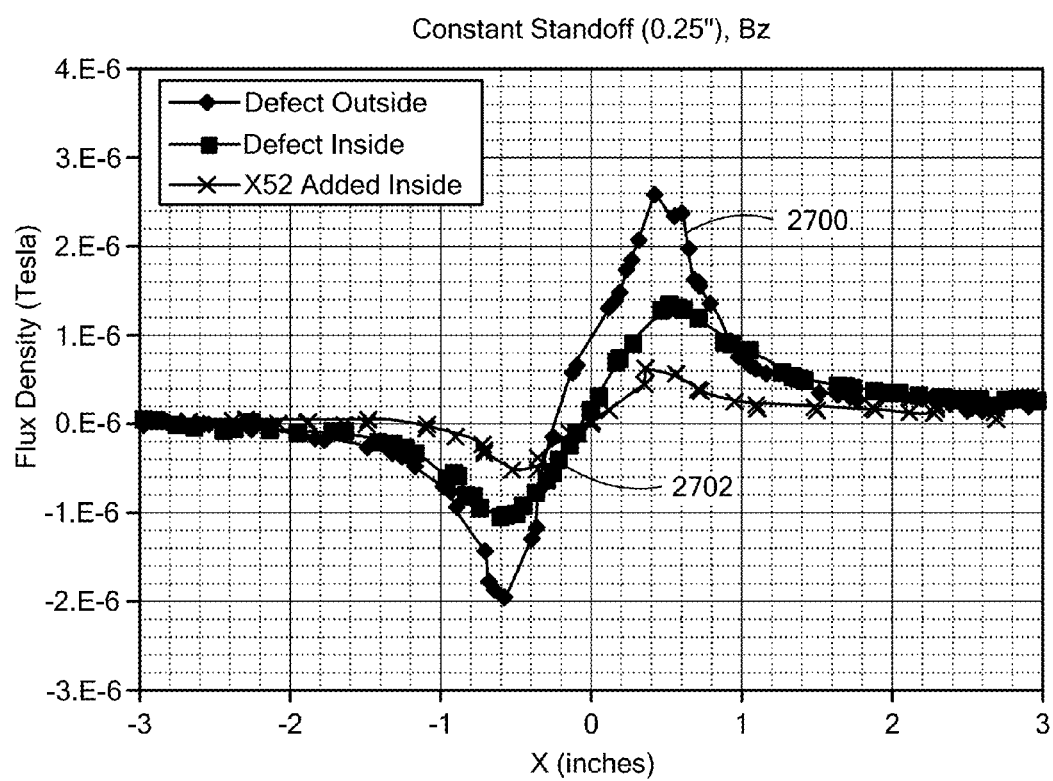
FIG. 27 is a graph illustrating differences in signal strength from a defect on an inside of a pipe and signal strength from a defect on an outside of the pipe, according to an embodiment of the present invention.

Defects within a pipe wall thickness or on an inside wall are necessarily further from magnetometers than defects on an outside wall of the pipe. However, simulations and tests indicate only a minor loss of signal from an internal defect, versus an external defect, as indicated in the plots in FIG. 27. Much of the reduction in signal amplitude is due to the larger standoff implicit in an internal defect as opposed to an external defect. Plot 2700 is for an external defect, and plot 2702 is for an internal defect.

As has been shown in the preceding discussion, many of the parameters in the detected signals have multiple, dependent sources. These dependencies should be understood and managed when performing detection and characterization of a defect. A relationship is that of sensor spacing. As implied in FIGS. 14 and 15, close spacing of the magnetometric sensors (magnetometers) is of interest. The spacing of the magnetometers relates to how small a defect (as measured along the surface) can be detected and characterized. Since the detection method relies on finding correlations with sine and cosine waves, it is necessary that there be a sufficient number of magnetometers along the sine wave to determine that it is truly a sine wave. In practice, sensors spaced 0.3 inch to 0.4 inch (7.6 to 10.2 mm) apart can be used to detect about 1-inch (25.4 mm) defects at a close (1 inch (25.4 mm) or less) standoff. As standoff increases or the surface dimensions decrease, the ability to reliably detect a defect decreases, with an increasing likelihood of missed detections or false alarms.

Temporal Defect Detection

Figure 28:
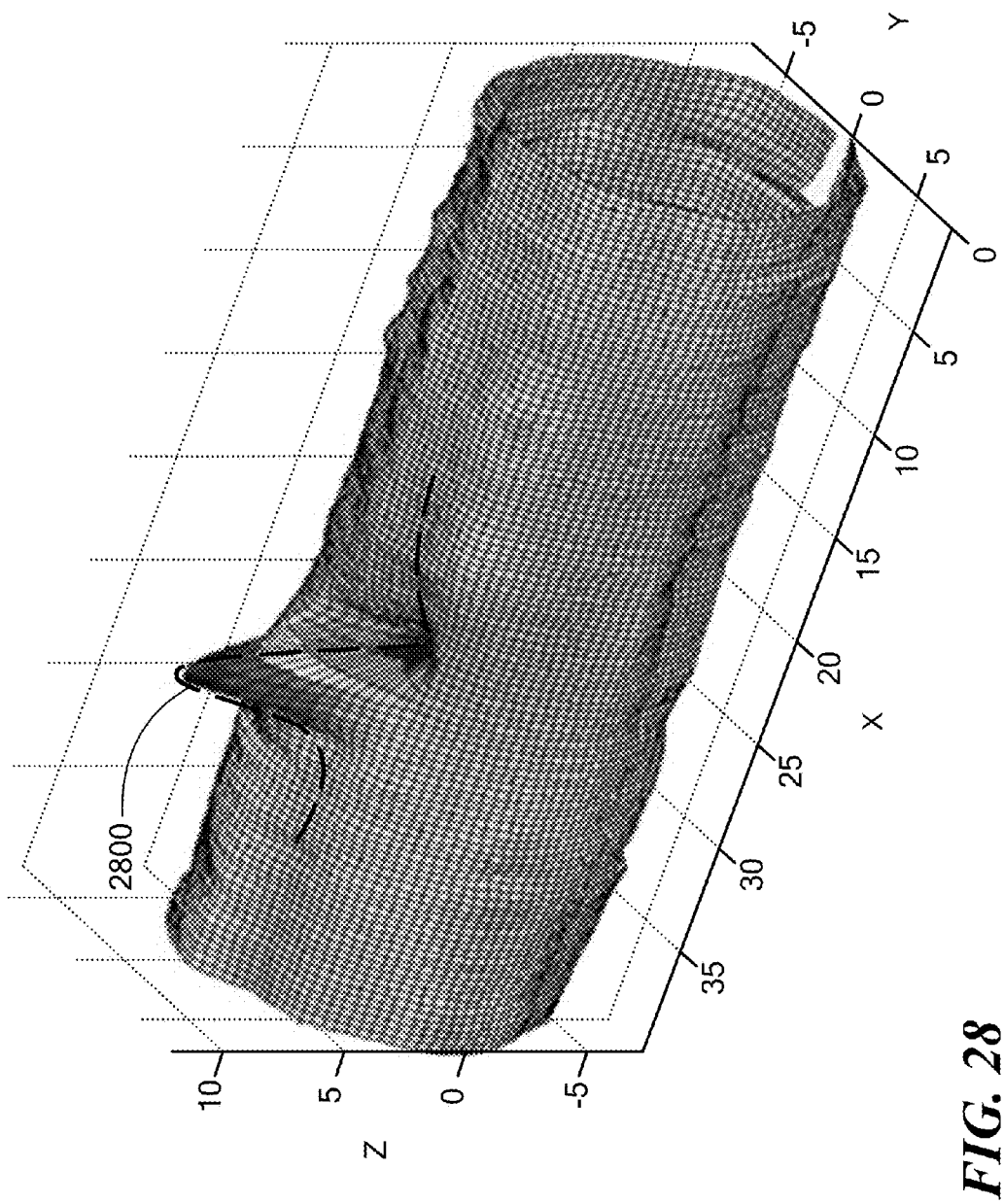
FIG. 28 is a surface plot of a result of a subtraction, showing the one axis of a magnetic field, according to a temporal analysis, according to an embodiment of the present invention.

As noted, in some embodiments of the present invention, rather than searching magnetometric data for signatures of defects, two datasets collected at different times are compared to detect defects. For example, one dataset may be collected when an item is new or at some other point in time. The second dataset is collected later. The two datasets are spatially correlated, and then magnetic field strengths in the second dataset are subtracted from spatially corresponding magnetic field strengths in the first dataset. These subtractions are performed per axis. FIG. 28 is a surface plot of the result of such a subtraction, showing the x axis of the magnetic field. A defect signature is clearly visible, as emphasized by dashed line 2800. The shape of the line 2800 is similar to the shape of the By curve in FIG. 4 and is, therefore, characteristic of a defect. In practice, the defect is found following this temporal subtraction by the basic method of the spatial analysis—one of fitting sine and cosine waves to confirm the remaining signal is a signature of a defect. As described above, with respect to spatial defect detection, spatial information about defects detected in each of the three axes may be combined to produce more accurate defect detection information. The approaches above for characterizing the defect (volume, area and depth) may be applied after this temporal method.

Physical Scanning an Item for Defects

Figure 29:
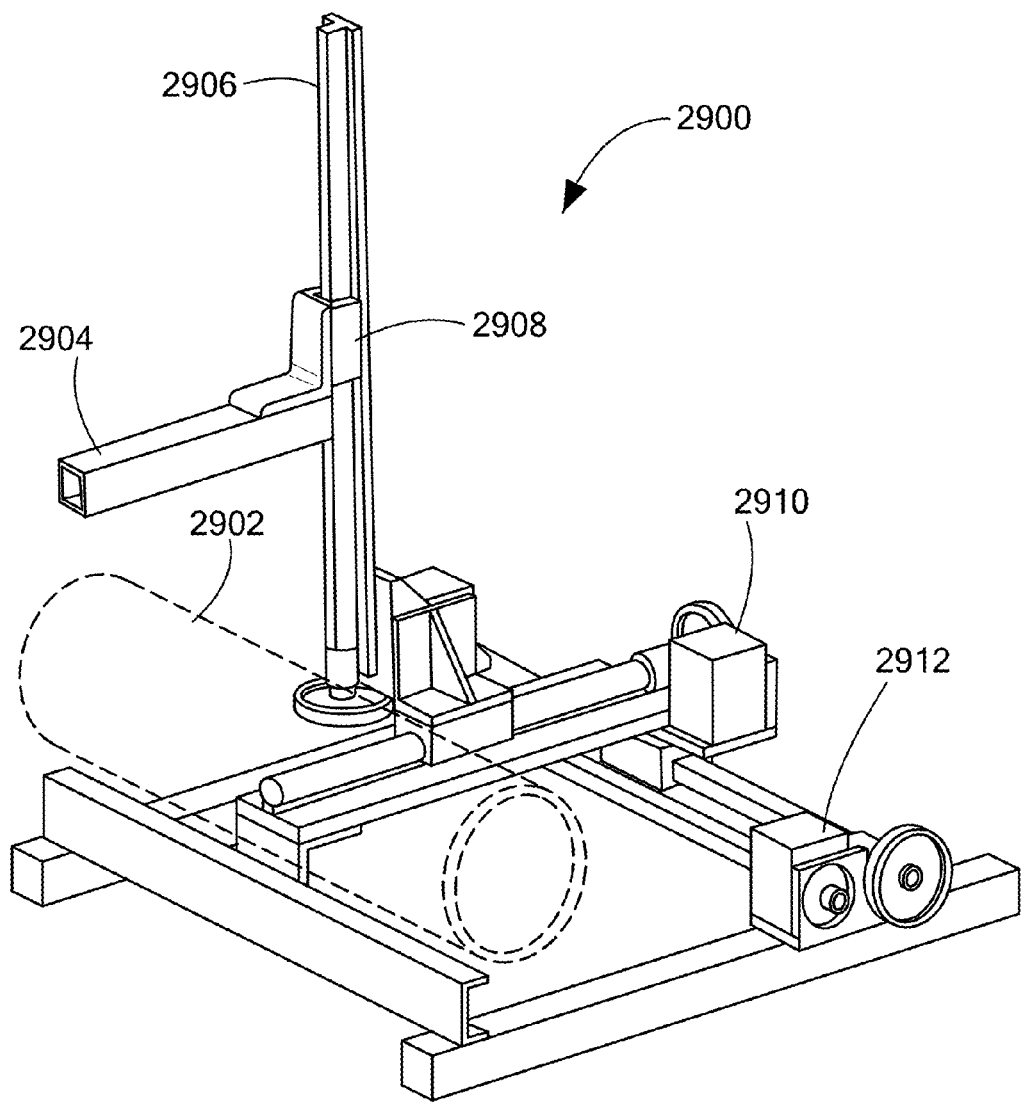
FIGS. 29 and 30 are perspective schematic views of apparatus for implementing physical scans of items, according to respective embodiments of the present invention.

As noted, magnetometric data about an item may be obtained by a fixed set of magnetometric sensors disposed about the item. Optionally or alternatively, the item may be physically scanned by a smaller set of magnetometric sensors than would be otherwise necessary to obtain the magnetometric data without scanning. The item may be scanned along its longitudinal axis or along any other suitable direction. FIG. 29 is a perspective illustration of a physical scanner 2900. An item 2902, such as a pipe, may be scanned by the scanner 2900. A single magnetometric sensor, a small group of magnetometric sensors or a one-dimensional array of magnetometric sensors 2904 is supported by a one-, two- or three-degree-of-freedom scanner arm 2906. A first linear motor 2908 positions the array of magnetometric sensors 2904 vertically a suitable distance from the item 2902. A second linear motor 2910 positions the array of magnetometric sensors 2904 along an axis perpendicular to the scanning axis. A third linear motor 2912 translates the array of magnetometric sensors 2904 along the scanning axis. Once a scan has been completed, the item may be rotated about the scan axis, and another scan may be performed. This process may be repeated until all desired portions of the item have been scanned.

Figure 30:
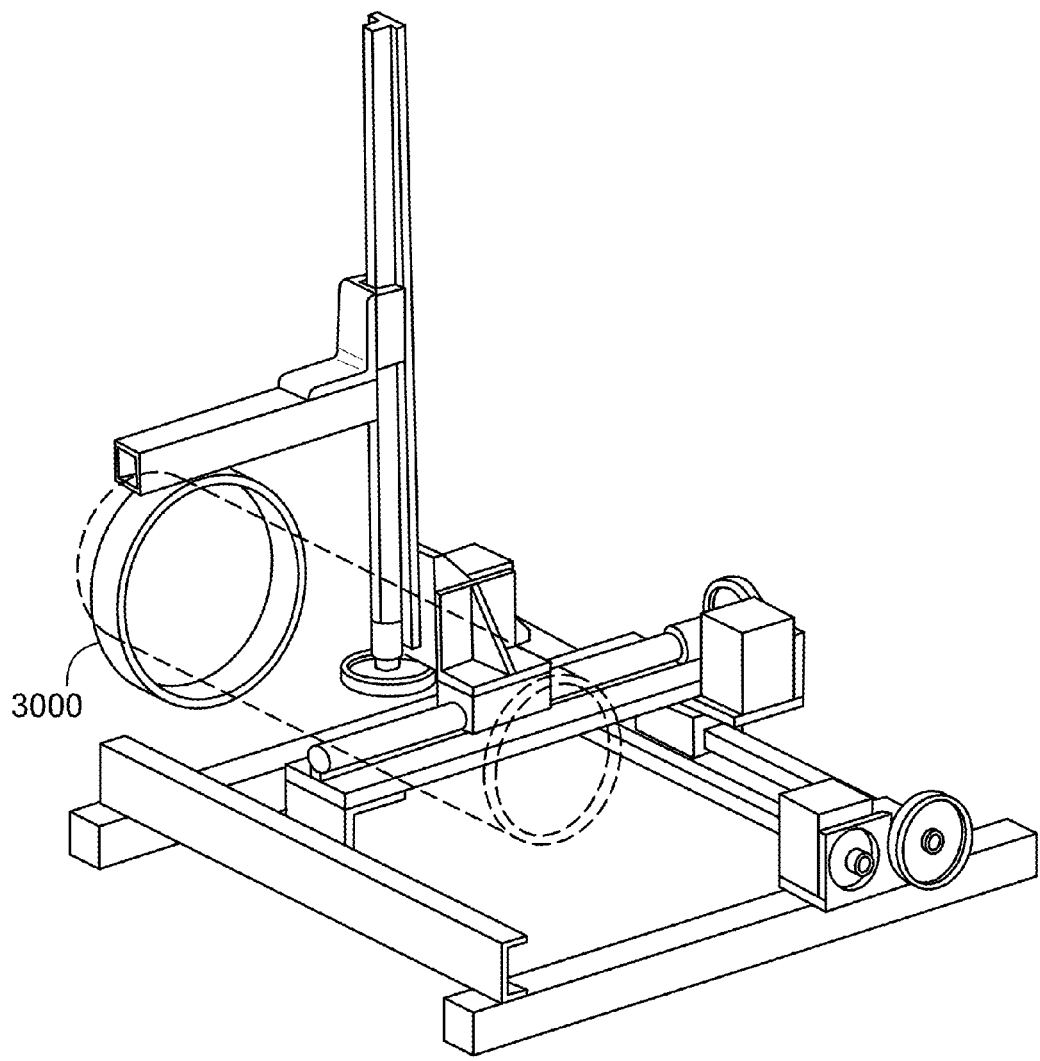

In another embodiment, perspectively illustrated in FIG. 30, a ring of magnetometric sensors is translated by the physical scanner 3002. In other embodiments, the scan may be two-dimensional. For example, with a suitable physical scanner, the item may be spiral scanned, raster scanned or scanned according to another path.

Figure 31:
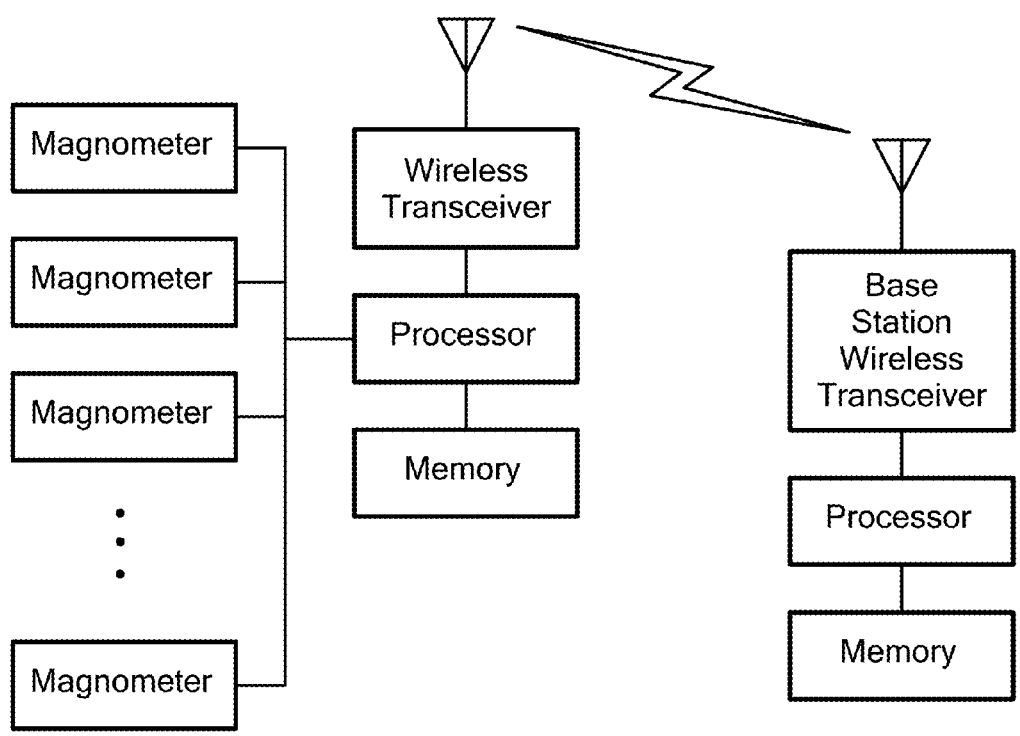
FIG. 31 is a schematic block diagram of a remote magnetometric sensor in wireless communication with a base station, according to an embodiment of the present invention.

The data collection from the magnetometers, the magnetic field mapper, the pattern matcher, and base station control functions and other functions described herein may be performed by a processor executing instructions stored in a memory, as schematically illustrated in FIG. 31.

While the invention is described through the above-described exemplary embodiments, modifications to, and variations of, the illustrated embodiments may be made without departing from the inventive concepts disclosed herein. Furthermore, disclosed aspects, or portions thereof, may be combined in ways not listed above and/or not explicitly claimed. Accordingly, the invention should not be viewed as being limited to the disclosed embodiments.

Although aspects of embodiments may be described with reference to flowcharts and/or block diagrams, functions, operations, decisions, etc. of all or a portion of each block, or a combination of blocks, may be combined, separated into separate operations or performed in other orders. All or a portion of each block, or a combination of blocks, may be implemented as computer program instructions (such as software), hardware (such as combinatorial logic, Application Specific Integrated Circuits (ASICs), Field-Programmable Gate Arrays (FPGAs) or other hardware), firmware or combinations thereof. Embodiments may be implemented by a processor executing, or controlled by, instructions stored in a memory. The memory may be random access memory (RAM), read-only memory (ROM), flash memory or any other memory, or combination thereof, suitable for storing control software or other instructions and data. Instructions defining the functions of the present invention may be delivered to a processor in many forms, including, but not limited to, information permanently stored on tangible non-writable storage media (e.g., read-only memory devices within a computer, such as ROM, or devices readable by a computer I/O attachment, such as CD-ROM or DVD disks), information alterably stored on tangible writable storage media (e.g., floppy disks, removable flash memory and hard drives) or information conveyed to a computer through a communication medium, including wired or wireless computer networks. Moreover, while embodiments may be described in connection with various illustrative data structures, systems may be embodied using a variety of data structures.

What is claimed is:

1. A method for detecting defects in a ferromagnetic material, the method comprising:
   disposing a plurality of magnetometers about a surface of the ferromagnetic material, wherein each magnetometer of the plurality of magnetometers is fixed in position, relative to the ferromagnetic material;
   using the plurality of magnetometers to sense a magnetic field generated by the ferromagnetic material at a first point in time;
   generating data points of a first two-dimensional map from the sensed magnetic field, each data point corresponding to a respective location on the surface of the ferromagnetic material and representing strength of the sensed magnetic field proximate the location at the first point in time;
   using the plurality of magnetometers to sense the magnetic field generated by the ferromagnetic material at a second point in time, later than the first point in time,
   generating data points of a second two-dimensional map from the sensed magnetic field, each data point corresponding to a respective location on the surface of the ferromagnetic material and representing strength of the sensed magnetic field proximate the location at the second point in time;
   subtracting the data points of the second two-dimensional map from spatially corresponding data points of the first two-dimensional map, thereby yielding a difference two-dimensional map;
   identifying, in the difference two-dimensional map, a plurality of data points that conform to a predefined spatial pattern of magnetic field strength; and
   outputting a location proximate the surface of the ferromagnetic material that corresponds to the plurality of data points.

2. A method according to claim 1, wherein the subtracting is performed per axis.

3. A method according to claim 1, further comprising estimating a volume of material missing from the ferromagnetic material at the location proximate the surface of the ferromagnetic material, based on amplitude of a feature represented by data in the plurality of data points.

4. A method according to claim 3, further comprising estimating a depth of the missing material, based on the estimated volume of missing material and length in two spatial directions of a feature represented by data in the plurality of data points.

5. A method according to claim 1, further comprising:
   determining amplitude of the magnetic field generated by the ferromagnetic material at a location distant from the location proximate the surface of the ferromagnetic material, based on at least one of the data points of the map; and
   estimating a volume of material missing from the ferromagnetic material at the location proximate the surface of the ferromagnetic material, according to amplitude of data in the plurality of data points and the amplitude of the magnetic field generated by the ferromagnetic material at a location distant from the location proximate the surface of the ferromagnetic material.

6. A method according to claim 5, further comprising estimating an area of the missing material, based on length in two spatial directions of a feature represented by data in the plurality of data points.

7. A method according to claim 5, further comprising estimating a depth of the missing material, based on the estimated volume of missing material and length in two spatial directions of a feature represented by data in the plurality of data points.

8. A method according to claim 1, wherein identifying the plurality of data points that conform to the predefined spatial pattern comprises fitting at least one of a sine curve and a cosine curve to the plurality of data points.

9. A method according to claim 1, further comprising:
calculating a plurality of spatial derivative values from the data points of the difference two-dimensional map; and wherein:
identifying the plurality of data points that conform to a predefined spatial pattern comprises identifying a plurality of data points that conform to the predefined spatial pattern of magnetic field strength from the plurality of spatial derivative values.

10. A method according to claim 1, wherein identifying the plurality of data points that conform to a predefined spatial pattern comprises identifying a plurality of data points that corresponds to a loss of a portion of the ferromagnetic material due to corrosion or erosion.

11. A method according to claim 1, wherein identifying the plurality of data points that conform to a predefined spatial pattern comprises identifying a plurality of data points that corresponds to a crack in the ferromagnetic material.

12. A method according to claim 1, wherein disposing the plurality of magnetometers comprises disposing the plurality of magnetometers on a cylindrical surface that surrounds an outer surface of the ferromagnetic material.

13. A method according to claim 1, wherein disposing the plurality of magnetometers comprises disposing the plurality of magnetometers on a cylindrical surface, such that the plurality of magnetometers defines a cylindrical lumen sized to receive the ferromagnetic material.

14. A method according to claim 1, wherein disposing the plurality of magnetometers comprises organizing the plurality of magnetometers as a two-dimensional array of magnetometers wrapped around the ferromagnetic material.

15. A method according to claim 1, wherein disposing the plurality of magnetometers comprises organizing the plurality of magnetometers as a plurality of rings of magnetometers, including spacing apart the plurality of rings of magnetometers longitudinally along the ferromagnetic material, such that each ring of the plurality of rings of magnetometers surrounds the ferromagnetic material.

16. A method according to claim 1, wherein:
each magnetometer of the plurality of magnetometers comprising three orthogonally oriented magnetometers;
generating the data points comprises generating the data points such that each data point of the respective first and second two-dimensional map represents strength of the sensed magnetic field in each of three orthogonal directions; and
identifying the plurality of data points that conform to the predefined spatial pattern comprises, for each of the three orthogonal directions, identifying a plurality of data points that conform to a predefined spatial pattern of magnetic field strength and a location proximate the surface of the ferromagnetic material that corresponds to the plurality of data points, thereby identifying three locations proximate the surface of the ferromagnetic material; the method further comprising:
calculating a refined location proximate the surface of the ferromagnetic material from the three identified locations; and wherein:
outputting the location comprises outputting the refined location.

17. A method according to claim 1, wherein disposing the plurality of magnetometers comprises disposing the plurality of magnetometers on a surface that extends less than circumferentially around an outer surface of the ferromagnetic material.

18. A method according to claim 1, wherein disposing the plurality of magnetometers comprises organizing the plurality of magnetometers as a two-dimensional array of magnetometers.

19. A method for detecting defects in a ferromagnetic material, the method comprising:
sensing a magnetic field generated by the ferromagnetic material at a first point in time;
generating data points of a first two-dimensional map from the sensed magnetic field, each data point corresponding to a respective location on the surface of the ferromagnetic material and representing strength of the sensed magnetic field proximate the location at the first point in time;
sensing the magnetic field generated by the ferromagnetic material at a second point in time, later than the first point in time;
generating data points of a second two-dimensional map from the sensed magnetic field, each data point corresponding to a respective location on the surface of the ferromagnetic material and representing strength of the sensed magnetic field proximate the location at the second point in time;
subtracting the data points of the second two-dimensional map from spatially corresponding data points of the first two-dimensional map, thereby yielding a difference two-dimensional map;
identifying, in the difference two-dimensional map, a plurality of data points that conform to a predefined spatial pattern of magnetic field strength; and
outputting a location proximate the surface of the ferromagnetic material that corresponds to the plurality of data points; wherein:
sensing the magnetic field comprises sensing the magnetic field with a plurality of magnetometers, each magnetometer of the plurality of magnetometers comprising three orthogonally oriented magnetometers;
generating the data points comprises generating the data points such that each data point of the respective first and second two-dimensional map represents strength of the sensed magnetic field in each of three orthogonal directions; and
identifying the plurality of data points that conform to the predefined spatial pattern comprises, for each of the three orthogonal directions, identifying a plurality of data points that conform to a predefined spatial pattern of magnetic field strength and a location proximate the surface of the ferromagnetic material that corresponds to the plurality of data points, thereby identifying three locations proximate the surface of the ferromagnetic material; the method further comprising:
calculating a refined location proximate the surface of the ferromagnetic material from the three identified locations; and wherein:
outputting the location comprises outputting the refined location.

* * * * *